United States Patent
McGarry

(12) 
(10) Patent No.: US 6,520,973 B1
(45) Date of Patent: *Feb. 18, 2003

(54) ANASTOMOSIS DEVICE HAVING AN IMPROVED NEEDLE DRIVER

(75) Inventor: Joshua E. McGarry, Cincinnati, OH (US)

(73) Assignee: Ethicon Endo-Surgery, Inc., Cinncinati, OH (US)

( * ) Notice: Subject to any disclaimer, the term of this patent is extended or adjusted under 35 U.S.C. 154(b) by 18 days.

This patent is subject to a terminal disclaimer.

(21) Appl. No.: 09/650,578

(22) Filed: Aug. 30, 2000

(51) Int. Cl.⁷ ............................................. A61B 17/04
(52) U.S. Cl. ................................................... 606/144
(58) Field of Search ................................. 606/143–145, 606/225, 232, 222, 223, 224, 226–231; 464/51–52, 57

(56) References Cited

U.S. PATENT DOCUMENTS

| | | | |
|---|---|---|---|
| 3,019,789 A | 2/1962 | Whitehill et al. ............ 128/305 |
| 3,196,706 A | * 7/1965 | Sevrence .................... 74/500.5 |
| 3,316,914 A | 5/1967 | Collito ........................ 128/334 |
| 3,981,307 A | 9/1976 | Borysko ...................... 128/339 |
| 3,990,321 A | * 11/1976 | Hurlow ...................... 74/500.5 |
| 4,112,708 A | * 9/1978 | Fukuda ........................ 464/174 |
| 4,124,027 A | 11/1978 | Boss ........................... 128/339 |
| 4,127,133 A | 11/1978 | Martinez ..................... 128/339 |
| 4,204,541 A | 5/1980 | Kapitanov ................... 128/334 |
| 4,285,292 A | * 8/1981 | Rathert et al. .............. 112/222 |
| 4,300,408 A | * 11/1981 | Yoshifuji ..................... 508/206 |
| 4,345,600 A | 8/1982 | Rothfuss ..................... 128/334 |
| 4,366,819 A | 1/1983 | Kaster ......................... 128/334 |
| 4,368,736 A | 1/1983 | Kaster ......................... 128/334 |
| 4,470,415 A | 9/1984 | Wozniak ..................... 128/334 |
| 4,593,693 A | 6/1986 | Schenck ..................... 128/334 |
| 4,657,019 A | 4/1987 | Walsh et al. ................. 128/334 |
| 4,749,114 A | 6/1988 | Green ......................... 227/19 |
| 4,773,420 A | 9/1988 | Green ......................... 128/334 |
| 4,803,984 A | 2/1989 | Narayanan et al. ......... 128/334 |
| 4,915,107 A | 4/1990 | Rebuffat et al. ............. 606/144 |
| 4,917,114 A | 4/1990 | Green et al. ................. 227/179 |
| 4,930,502 A | 6/1990 | Chen .......................... 606/150 |
| 4,931,057 A | 6/1990 | Cummings et al. ......... 606/153 |
| 4,945,920 A | * 8/1990 | Clossick ...................... 600/564 |
| 4,997,439 A | 3/1991 | Chen .......................... 606/216 |
| 5,041,127 A | 8/1991 | Troutman .................... 606/223 |
| 5,041,128 A | 8/1991 | Korthoff ...................... 606/224 |

(List continued on next page.)

FOREIGN PATENT DOCUMENTS

| | | | | |
|---|---|---|---|---|
| DE | 19704261 A1 | 8/1998 | ........... A61B/17/11 |
| EP | 0885595 A1 | 12/1998 | ......... A61B/17/115 |
| EP | 0956825 A2 | 11/1999 | ........... A61B/17/11 |
| WO | WO99/37218 | 7/1999 | ........... A61B/17/08 |
| WO | WO99/40851 | 9/1999 | |
| WO | WO99/45852 | 9/1999 | ........... A61B/17/11 |

*Primary Examiner*—David O. Reip
*Assistant Examiner*—D Jacob Davis

(57) ABSTRACT

In accordance with the present invention, there is provided an anastomosis device for attaching a first hollow vessel to a second hollow vessel. The device includes a handle for holding the device, and a head assembly, attached to the handle, for holding the first and second hollow vessels adjacent to each other. The head assembly having a distal end, a proximal end and a longitudinal axis therebetween. The device further includes a needle guide disposed longitudinally along the head assembly adjacent to the vessels, and a helical needle, having a suture attached to a proximal end thereof, disposed within the head assembly at its proximal end. The device has an actuator on the handle for actuating a needle driver. The needle driver is coupled to the head and includes a flexible rotatable member operated by the actuator, for rotating and driving the needle distally along the needle guides and through the first and second hollow vessels. The rotatable member is made from an inner shaft, an intermediate coiled spring surrounding the shaft, and an outer wire mesh surrounding the coiled spring.

14 Claims, 25 Drawing Sheets

U.S. PATENT DOCUMENTS

| | | | |
|---|---|---|---|
| 5,051,107 A | 9/1991 | Korthoff | 606/224 |
| 5,059,212 A | 10/1991 | Korthoff | 606/224 |
| 5,084,063 A | 1/1992 | Korthoff | 606/226 |
| 5,089,008 A | 2/1992 | Chen | 606/216 |
| 5,089,010 A | 2/1992 | Korthoff | 606/224 |
| 5,089,011 A | 2/1992 | Korthoff | 606/224 |
| 5,116,358 A | 5/1992 | Granger | 606/224 |
| 5,123,911 A | 6/1992 | Granger et al. | 606/224 |
| 5,123,914 A * | 6/1992 | Cope | 606/108 |
| 5,133,738 A * | 7/1992 | Korthoff et al. | 606/224 |
| 5,139,514 A | 8/1992 | Korthoff et al. | 606/224 |
| 5,141,520 A * | 8/1992 | Goble et al. | 606/104 |
| 5,156,615 A | 10/1992 | Korthoff et al. | 606/224 |
| 5,188,636 A | 2/1993 | Fedtov | 606/144 |
| 5,226,912 A | 7/1993 | Kaplan et al. | 606/224 |
| 5,245,887 A * | 9/1993 | Tanaka et al. | 74/500.5 |
| 5,259,845 A | 11/1993 | Korthoff | 606/227 |
| 5,356,424 A | 10/1994 | Buzerak et al. | 606/223 |
| 5,383,902 A | 1/1995 | Carpentiere et al. | 606/224 |
| 5,403,345 A | 4/1995 | Spingler | 606/224 |
| 5,411,481 A | 5/1995 | Allen et al. | 606/144 |
| 5,425,737 A | 6/1995 | Burbank et al. | 606/144 |
| 5,426,995 A * | 6/1995 | Maennle | 73/118.1 |
| 5,520,703 A | 5/1996 | Essig et al. | 606/148 |
| 5,545,148 A * | 8/1996 | Wurster | 604/223 |
| 5,562,685 A | 10/1996 | Mollenauer et al. | 606/144 |
| 5,571,090 A | 11/1996 | Sherts | 604/144 |
| 5,695,504 A | 12/1997 | Gifford, III et al. | 606/153 |
| 5,702,048 A | 12/1997 | Eberlin | 227/177.1 |
| 5,709,335 A | 1/1998 | Heck | 227/176.1 |
| 5,732,872 A | 3/1998 | Bolduc et al. | 227/176.1 |
| 5,769,858 A * | 6/1998 | Pearson et al. | 600/585 |
| 5,802,929 A * | 9/1998 | Furukawa et al. | 74/500.5 |
| 5,807,395 A * | 9/1998 | Mulier et al. | 604/22 |
| 5,817,113 A | 10/1998 | Gifford, III et al. | 606/153 |
| 5,836,955 A * | 11/1998 | Buelna et al. | 606/144 |
| 5,868,763 A | 2/1999 | Spence et al. | 606/153 |
| 5,881,943 A | 3/1999 | Heck et al. | 227/176.1 |
| 5,883,698 A | 3/1999 | Kimura | 355/38 |
| 5,893,369 A | 4/1999 | LeMole | 606/184 |
| 5,904,696 A * | 5/1999 | Rosenman | 606/151 |
| 5,904,697 A | 5/1999 | Gifford, III et al. | 606/155 |
| 5,916,226 A | 6/1999 | Tozzi | 606/153 |
| 5,935,138 A * | 8/1999 | McJames et al. | 606/139 |
| 5,944,730 A | 8/1999 | Nobles et al. | 606/151 |
| 5,951,576 A | 9/1999 | Wakabayashi | 606/151 |
| 5,957,363 A | 9/1999 | Heck | 227/19 |
| 5,972,024 A | 10/1999 | Northrup, III et al. | 606/232 |
| 5,976,159 A | 11/1999 | Bolduc et al. | 606/142 |
| 6,003,403 A * | 12/1999 | Klippert et al. | 403/379.1 |
| 6,015,416 A | 1/2000 | Stefanchik et al. | 606/144 |
| 6,209,415 B1 * | 4/2001 | Uneme et al. | 74/500.5 |
| 2001/0044619 A1 * | 11/2001 | Altman | 604/619 |

\* cited by examiner

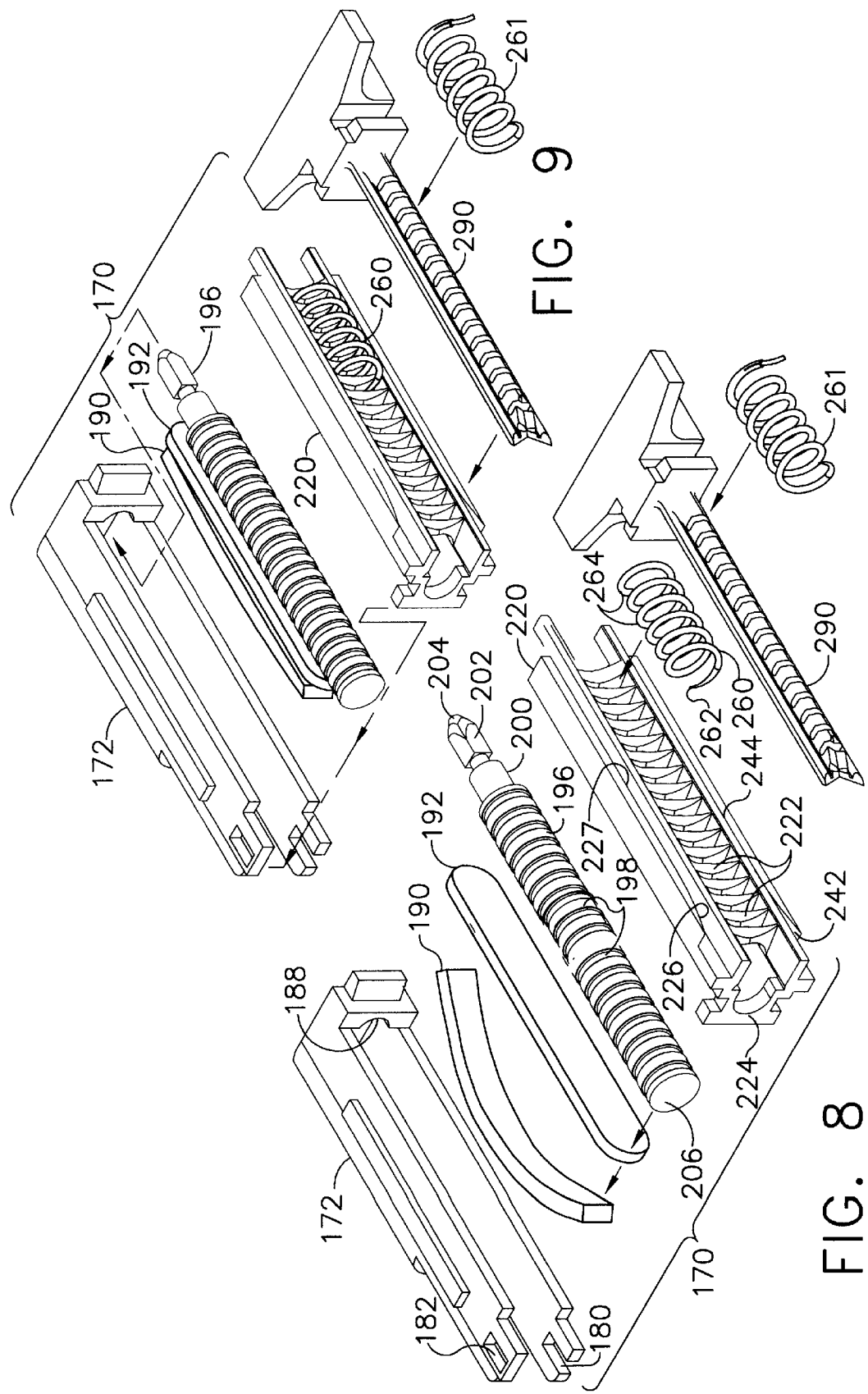

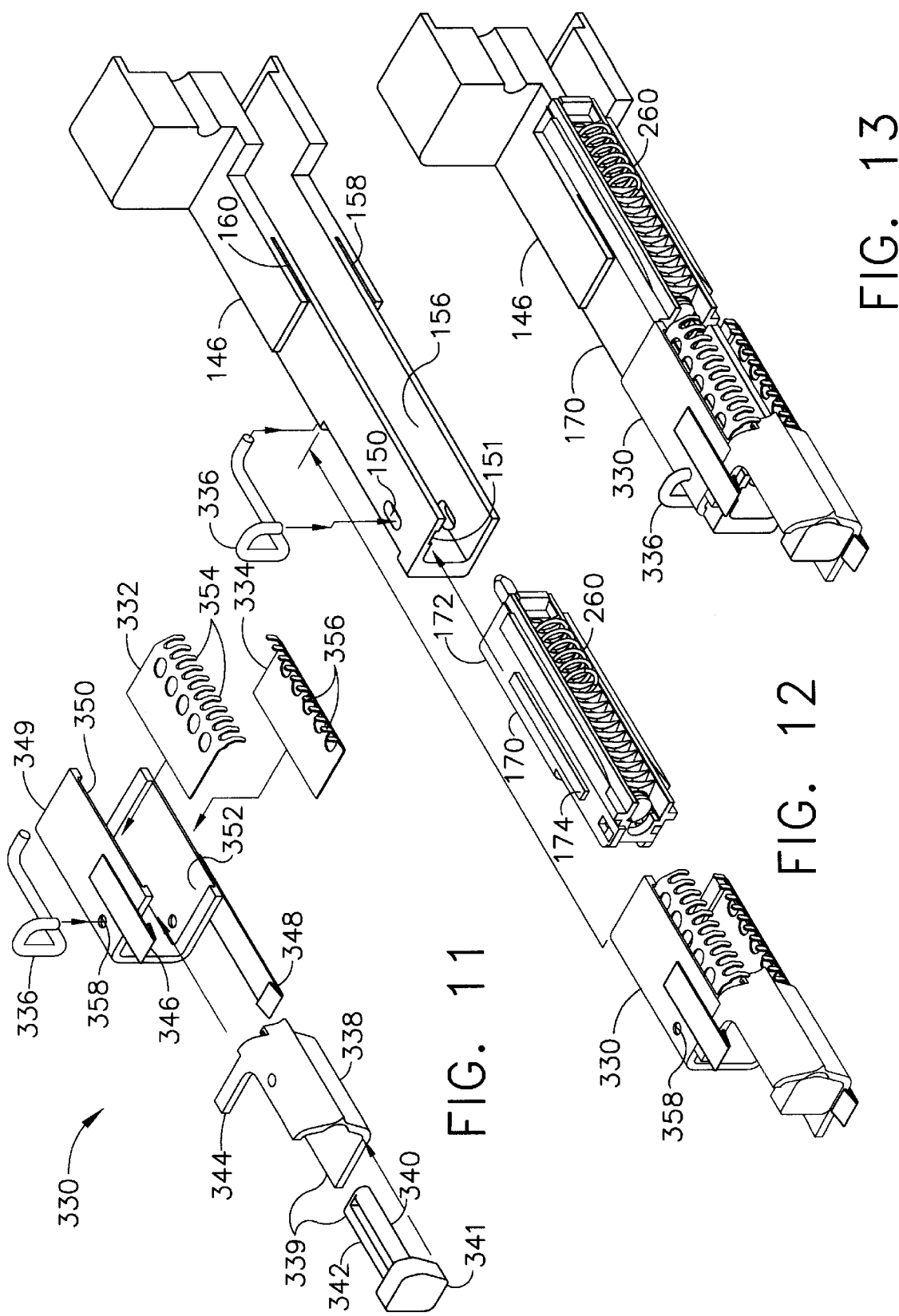

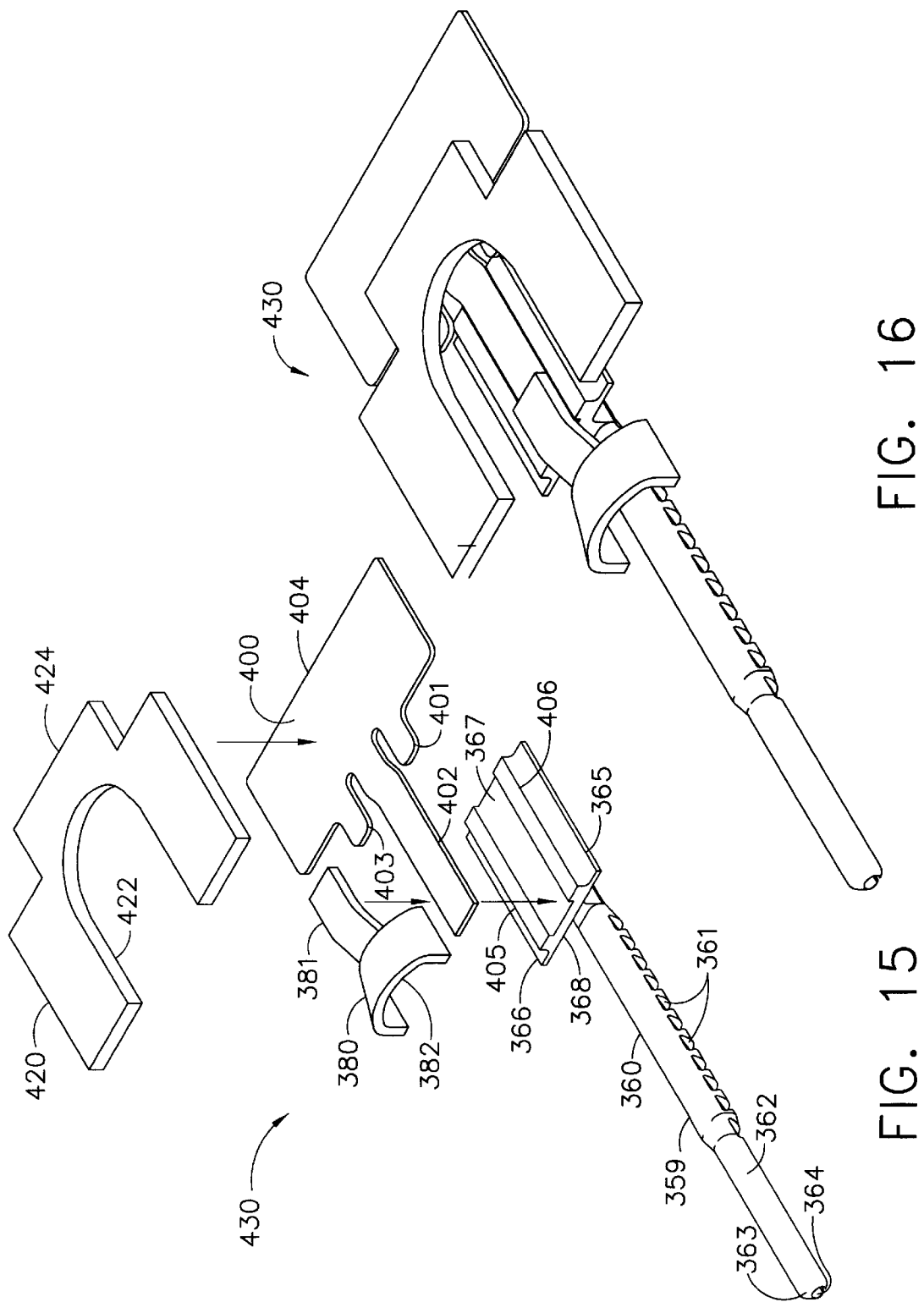

ANASTOMOSIS DEVICE HAVING AN IMPROVED NEEDLE DRIVER

FIELD OF THE INVENTION

The present invention relates, in general, to devices and methods that facilitate the anastomosis of hollow organs of the body. More particularly, it relates to vascular anastomosis devices incorporating sutures for joining a graft blood vessel to a target blood vessel such as the aorta or coronary artery.

BACKGROUND OF THE INVENTION

Surgically forming a passage between lumens of two normally distinct organs is a critical part of many surgical procedures. In a coronary artery bypass graft (CABG) procedure, the surgeon uses a graft vessel harvested from the patient to connect a blood supply vessel such as the aorta to the diseased coronary artery on the heart. An anastomosis is made on both the distal and proximal ends of the graft vessel. Surgeons typically use the saphenous vein of the leg or the radial artery of the arm or both, in multiple bypass cases. In an alternative procedure, the internal mammary artery (IMA) is used as a graft vessel. In this procedure the IMA is temporarily clamped, severed at a location allowing enough length to be redirected towards the heart, dissected from the chest wall and arterial side branches, and then the distal end (pedicle) is sutured to the left anterior descending coronary artery (LAD) to improve or restore blood flow to the left ventricle of the heart.

For the grafting procedures mentioned above, the surgeon performs an end-to-side type of vascular anastomosis. That is, the surgeon attaches the open end of the graft vessel to the side of the target vessel. However, surgeons also perform other types of anastomoses. Surgeons commonly use an end-to-end type of anastomosis for joining together larger hollow organs such as bowel, and for some heart bypass procedures where the arterial flow is completely occluded by the stenosis in the diseased artery.

Some surgeons choose to complete all the proximal anastomoses to the aorta before commencing the distal anastomoses to the coronary arteries. In contrast, others choose to complete the distal anastomoses first. Regardless of the order, when undertaking a distal anastomosis to the coronary artery, it is important to atraumatically hold the vessel graft steady and adjacent the coronary artery, with a minimum of visual and surgical obstruction by instruments in the narrow operative field.

Currently surgeons perform each vascular anastomosis by hand suturing with a tiny, curved needle and very fine suture filament. Such a suturing method, however, is very time consuming and requires several minutes per anastomosis, even for an experienced surgeon. In some cases the blood flow in the newly joined vessels may be poor, and the surgeon must remove the stitches and repeat the suturing procedure. In surgical procedures involving multiple bypass grafts, the total time required for suturing is very substantial, putting the patient at risk and increasing the cost of the surgical procedure.

In a preferred type of suturing method for the anastomosis of blood vessels, the surgeon passes a needle through the wall of the first vessel (such as the coronary artery) from the inside to the outside, and then passes it from the outside to the inside of the second vessel (such as the graft vessel), so that when the suture is drawn tight, the inside walls of the vessels come together, intima-to-intima. This is to ensure that the vessels heal together properly with a smooth layer of endothelial cells formed on the inside of the anastomosis. The surgeon typically places a single stitch in this manner at each of the heel and toe locations of the anastomosis, and then makes a running stitch on each half of the anastomosis between the heel and toe.

For the standard CABG procedure, the surgeon accesses the heart through a median sternotomy in which the rib cage is split longitudinally on the midline of the chest, and the left and right rib cages are spread apart. In recent years, surgeons have been using other means of access to the heart to reduce the size of the surgical wound created. In a surgical procedure known as a MIDCAB (Minimally Invasive Direct Coronary Artery Bypass), the surgeon accesses the heart by using a small, left thoracotomy (incision between the ribs on the left chest) directly above the heart. In this procedure, the surgical opening and visibility of the heart are significantly reduced, and hand suturing is more difficult than when using a median sternotomy. Other new developments in the surgical procedures have made conventional suturing even more difficult. For example, some surgeons now perform bypass surgery on beating hearts to avoid the complications associated with using a heart lung bypass machine.

The literature contains disclosures of a number of devices for augmentation of the suturing techniques. These devices attempt with varying degrees of success to reduce the difficulty in repeatedly passing a needle and thread through the vascular walls. Examples include the following: U.S. Pat. No. 5,571,090 issued to Sherts on Nov. 5, 1996; U.S. Pat. No. 4,803,984 issued to Narayanan on Feb. 14, 1989; and U.S. Pat. No. 5,545,148 issued to Wurster on Aug. 13, 1996. However, these devices have a number of disadvantages. In Sherts and Narayanan, the individual stitches must be made one at a time and therefore the procedure is still tedious and time consuming. The working ends of the Wurster and Sherts devices appear to obstruct the view of the needle tip so precise placement of the stitch might be difficult in some situations.

When suturing tiny blood vessels together, the surgeon must minimize manipulation of the graft and the target vessels to prevent damaging them. This ensures that the vessels heal together properly and a smooth passage between them is created. Usually in a conventional bypass procedure the surgeon applies a surgical clamp upstream (proximal) to the anastomotic location on the coronary artery to stop blood flow there. Applying surgical clamps may injure the artery and compromise the long term viability of the vessel to maintain blood flow. Applying surgical clamps may also dislodge plaque adhered on the intima of the lumen of the diseased vessel, creating emboli that could migrate into the systemic circulation and seriously injure or kill the patient.

An example of a device which simplifies the anastomosis procedure for the physician is shown in U.S. Pat. No. 6,015,416 issued to Stefanchik et al on Jan. 18, 2000 (hereinafter Stefanchik), which is hereby incorporated herein by reference. Stefanchik discloses a handheld, surgical device that addresses the aforementioned considerations. The device in Stefanchik facilitates a sutured anastomosis of very small hollow organs such as blood vessels while maintaining blood flow in the vessels. The device in Stefanchik comprises a first member having a first prong for entering a first vessel and a second prong for entering the wall of a second vessel. The device further comprises a second member having a plow for incising at least one of the vessels so as to create a passageway between the vessels. A frame is provided for coupling the first member and the second member together in operational engagement. The second member further includes a plurality of needle paths on either side of the plow for guiding a pair of helical needles with attached sutures through the walls of the vessels on either side of the passageway. The device also includes a means for driving the helical needles so as to attach the vessels together. The device in Stefanchik requires minimal manipulation of the blood vessels and joins the vessels together intima-to-intima. The device in Stefanchik may be used during traditional, open cardiac procedures (CABG) as well as in minimally invasive procedures such as MIDCAB procedures.

A shortcoming of the device in Stefanchik is the conventional type of attachment between the suture filament and the helical needle. The suture filament used is a size 7-0 propylene monofilament, and is swaged directly to the stainless steel needle without any kind of strain relieving interface. As each helical needle rotates through the vessel walls, the suture filament twists and pulls at the needle attachment and risk of suture filament breakage is significant. What is needed is a stress relieving interface at the needle-suture attachment.

Although stress relieving interfaces are widely used in the electronics industry for attachment of connectors to wires or cords, the novel application of stress relieving interfaces to surgical needle-suture attachments has not been available prior to the present invention. Several references are available describing inventions for controlled suture release so that the needles may be pulled off the suture by applying forces in relatively uniform and consistent ranges. Examples of controlled release sutures are the following: U.S. Pat. No. 4,124,027 issued to Boss on Nov. 7, 1978; U.S. Pat. No. 5,089,010 issued to Korthoff on Feb. 18, 1992; and U.S. Pat. 5,403,345 issued to Spingler on Apr. 4, 1995. However, these inventions and the others cited in the references are designed specifically for lowering the force required to separate the needle from the suture. There are no references that describe devices or methods for preventing suture breakage at the suture-needle attachment when the suture is highly stressed due to twisting and pulling at the needle attachment.

A second shortcoming of the device disclosed in Stefanchik is poor visibility of one of the two hollow organs being joined together. Stefanchik describes placement of a first prong for entering a wall of a first hollow organ (for example, a graft vessel) and a second prong for entering the wall of a second hollow organ (for example, a coronary vessel on the heart). The second prong is attached to an implement, which obstructs the view of the second hollow organ while the second prong is placed into the wall of the second hollow organ. What is needed is a means for retracting the implement apart from the second prong so that the operator has improved visibility of the second hollow organ during placement of the second prong into the wall of the second hollow organ.

A third shortcoming of the device disclosed in Stefanchik is the ease of removing the two needles from the implement after the stitches are made to join the two hollow organs together, and for drawing the two sutures through the two hollow organs to provide enough free length of suture for tying a knot to complete the anastomosis. For the device in Stefanchik, it is necessary to use a surgical grasping tool to grasp each needle, release it from the implement, and pull directly on the needle to draw suture through the two hollow organs. Since the needles are very small and partially obstructed by the implement, it may be difficult for the operator to easily grasp the needle in this manner, especially during an endoscopic surgical procedure. What is needed is a needle receiver for each needle within the element, so that at the end of the actuation of the device in Stefanchik, the needle receiver may be grasped easily by a surgical grasping tool and withdrawn from the implement of the device while pulling the suture attached to the needle to provide a sufficient length of suture for knot tying.

For the device in Stefanchik, it is necessary that the implement be temporarily attached to a bodily organ, such as the heart, during the operational sequence of the device and that the drive unit for driving the implement be handheld by an operator during the procedure. Another desirable refinement to the device in Stefanchik would be to use a commercially available, sheathed cable particularly adapted for transmitting rotational and translational force from a drive unit to the implement of the device. By using a commercially available, sheathed cable, the cost to manufacture the surgical device could be reduced. Improving efficiency of force transfer would allow smoother and easier operation of the surgical device.

SUMMARY OF THE INVENTION

In accordance with the present invention, there is provided an anastomosis device for attaching a first hollow vessel to a second hollow vessel. The device includes a handle for holding the device, and a head assembly, attached to the handle, for holding the first and second hollow vessels adjacent to each other. The head assembly having a distal end, a proximal end and a longitudinal axis therebetween. The device further includes a needle guide disposed longitudinally along the head assembly adjacent to the vessels, and a helical needle, having a suture attached to a proximal end thereof, disposed within the head assembly at its proximal end. The device has an actuator on the handle for actuating a needle driver. The needle driver is coupled to the head and includes a flexible rotatable member operated by the actuator, for rotating and driving the needle distally along the needle guides and through the first and second hollow vessels. The rotatable member is made from an inner shaft, an intermediate coiled spring surrounding the shaft, and an outer wire mesh surrounding the coiled spring.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 8 is an exploded isometric view of a right roller assembly 170, which is part of head assembly 100 shown in FIG. 7;

FIG. 9 is an exploded isometric view of right roller assembly 170 shown in FIG. 8, with a right leaf spring 190 and a right spring plate 192 shown in closer alignment with a right roller 196;

FIG. 11 is an exploded isometric view of a right tissue holder 330, which is part of head assembly 100 shown in FIG. 7;

FIG. 12 is an isometric view of right tissue holder 330, right roller assembly 170, and a right frame 146 shown in alignment prior to assembly;

FIG. 13 is an isometric view of right tissue holder 330, right roller assembly 170, and right head frame 146 shown assembled;

FIG. 15 is an exploded isometric view of an upper pin assembly 430, which is part of head assembly 100 shown in FIG. 7;

FIG. 16 is an isometric view of assembled, upper pin assembly 430 shown in FIG. 15;

DETAILED DESCRIPTION OF THE INVENTION

In the following detailed description of the present invention, the applicants provide a description of how the invention is used to create a modified end-to-side anastomosis between two blood vessels. The present invention may also be used to create conventional end-to-side, side-to-side and end-to-end anastomoses, and is not limited to only blood vessels, but may be used also for joining other types of hollow organs.

Figure 1:
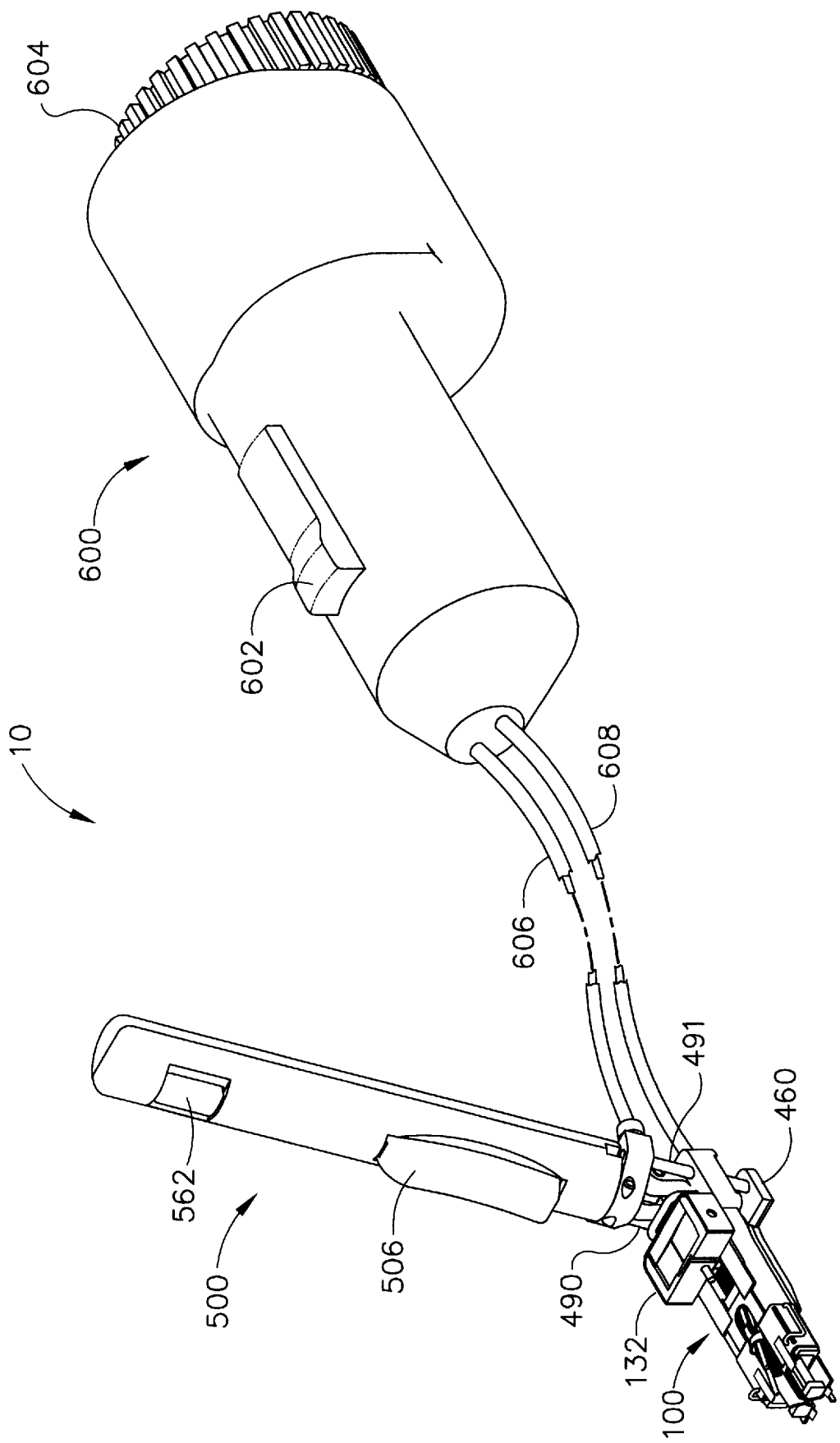
FIG. 1 is an isometric view of the present invention, a surgical device 10.

Referring now to the drawings wherein like numerals indicate the same element throughout the views, there is shown in FIG. 1 a preferred embodiment of the present invention, a surgical device 10. Device 10 generally comprises a handle 500, a head assembly or member 100, shown in a first position, and a drive unit 600. Head assembly 100 is operationally connected to handle 500 by a block assembly 132, which slides along a right rail 490 and a left rail 491 affixed to handle 500. A lower pin assembly 460, or arm, is attached to right rail 490 and left rail 491. Handle 500 includes a first actuator 506 and a second actuator 562. Drive unit 600 operationally connects to head assembly 100 by a right drive cable, or flexible rotatable member, 606 and a left drive cable, or flexible rotatable member, 608. Drive unit 600 includes a third actuator 602 and a fourth actuator 604, which is rotatable only in one direction.

Figure 2:
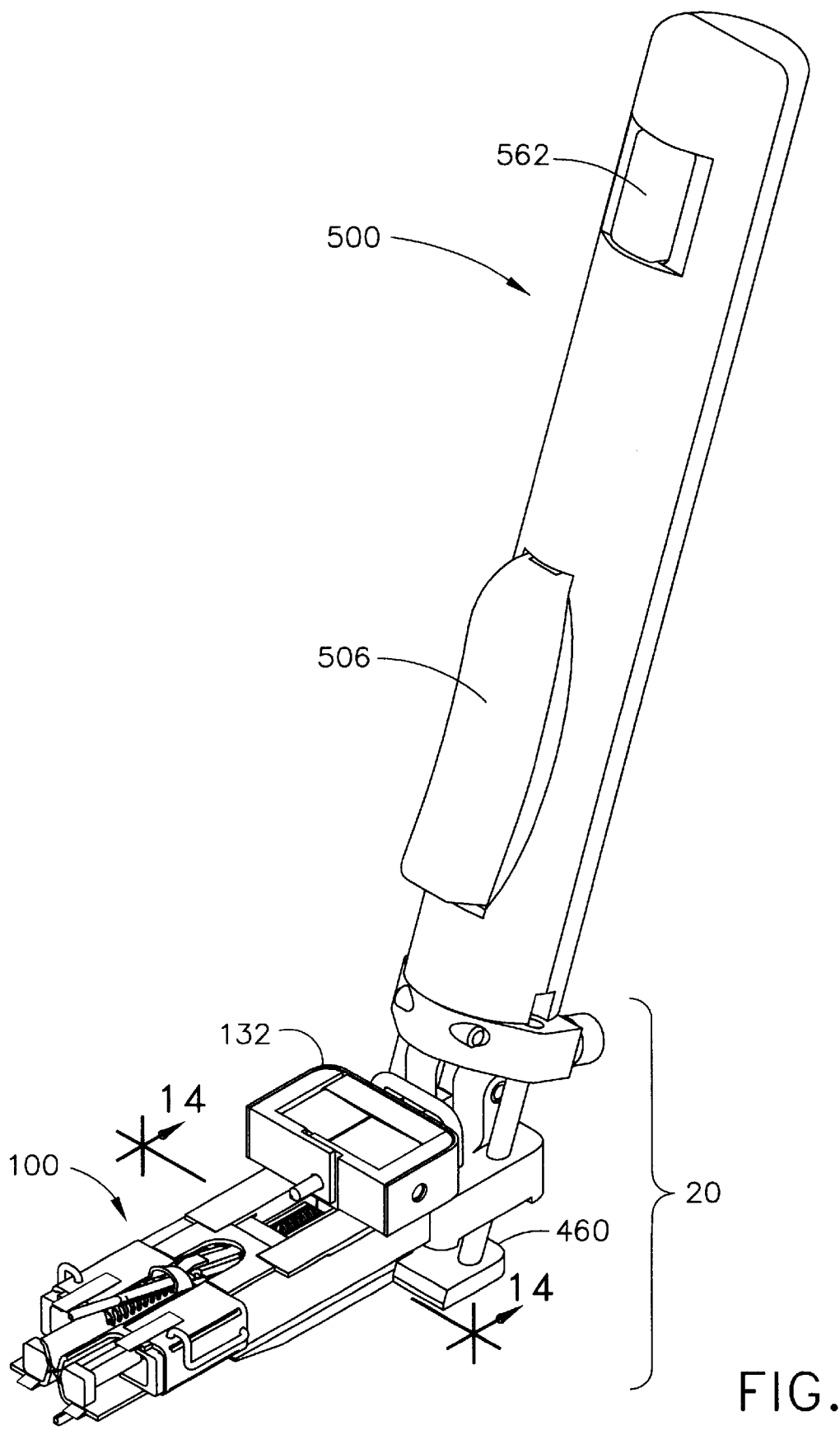
FIG. 2 is an isometric view of a head assembly 100 and a handle 500 of surgical device 10 shown in FIG. 1.

FIG. 2 is an isometric view of head assembly 100 in the first position and handle 500. When an operator completely depresses first actuator 506 on handle 500, head assembly 100 laterally moves to a second position closer to lower pin assembly 460 and member 100 and locks into place. When an operator depresses second actuator 562 on handle 500, head assembly 100 returns to the first position. Head assembly 100, block assembly 132, and lower pin assembly 460 also comprise what is referred to as a working portion 20 of the present invention.

Figure 3:
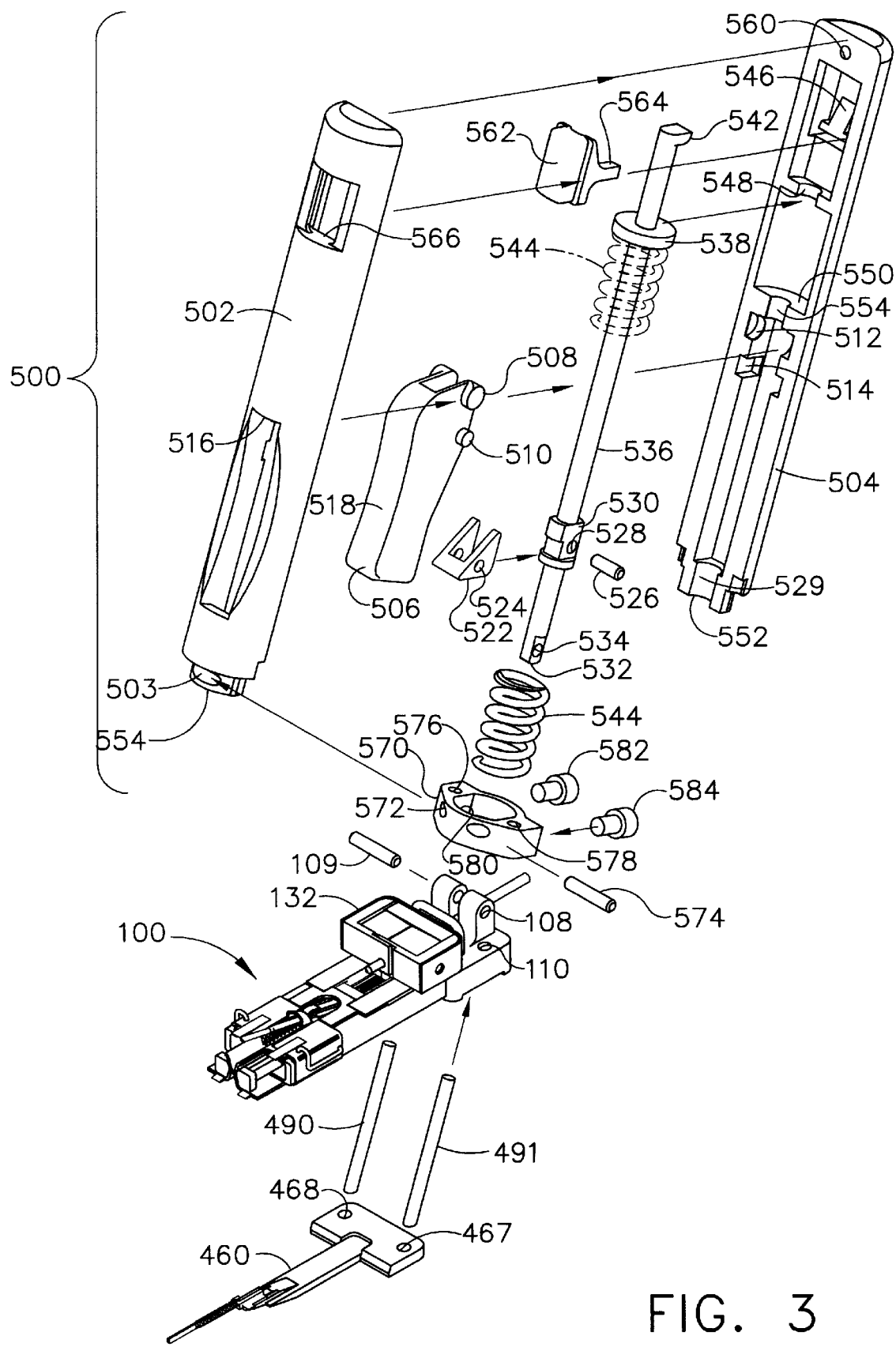
FIG. 3 is an exploded isometric view of head assembly 100 and handle 500 shown in FIG. 2.

FIG. 3 contains an exploded isometric view of the components of handle 500, and includes head assembly 100 and lower pin assembly 460 separated from handle 500. Right rail 490 and left rail 491 fixedly attach to a right rail hole 468 and a left rail hole 467, respectively, of lower pin assembly 460. Left rail 491 slidably passes through a left block hole 110 of block assembly 132 and into a left collar hole 578 of a collar 570. A left collar screw 584 screws into collar 570 and attaches left rail 491 to collar 570. Similarly, right rail 490 slidably assembles into block assembly 132 and fixedly attaches to a right collar hole 576 of collar 570 by a right collar screw 582. Handle 500 further includes a rod 536 for moving head assembly 100 up and down. A return spring 544 assembles over rod 536 and bears against a flange 538 as shown in a phantom view of return spring 544. Return spring 544 also pushes against a spring ledge 550 in a second handle half 504, thus tending to urge rod 536 in the proximal (upward) direction. Rod distal end 532 passes through a collar opening 580 and pivotally attaches to head assembly 100 by insertion of a block pin 109 through a block hole 108 and a rod hole 534 of rod 536 (pivot assembly). A wedge element 522 is pivotally attached to a bushing 530 connected to rod 536 by a wedge pin 526 inserted through a bushing hole 528 and a wedge hole 524. When an operator presses a first surface 518 of first actuator 506, wedge element 522 is pushed in the distal (downward) direction to move head assembly 100 closer to lower pin assembly 460. First actuator 506 includes a first axle 508 for pivoting in a first axle recess 512 in second handle half 504. First actuator 506 also includes a first stop post 510 that limits the travel of first actuator 506 by hitting a first stop recess 514 in first handle half 504. Rod 536 reciprocates longitudinally in a lower bearing surface 529, a middle bearing surface 554, and a upper bearing surface 548 of second handle half 504. The proximal end of rod 536 is adapted with a hook 542 for engaging with a latch 546 in second handle half 504 so that head assembly 100 may be held in the second position when first actuator 506 has been fully depressed. Rod 536 is released by depressing second actuator 562 having a latch release arm 564 that disengages latch 546 from hook 542, thus allowing head assembly 100 to return to the first position. A first handle half 502 attaches to second handle half 504 by any one of numerous fastening means well known in the art, and a handle fastener hole 560 is provided in the proximal end of second handle half 504. A first and a second distal end half, 552 and 554, of first and second handle halves, 502 and 504, are held together within collar opening 580 and to block assembly 132 by a collar pin 574 passing through a collar pin hole 572 of collar 570, and engaging with a collar pin slot 503 in first handle half 502. When handle 500 is fully assembled, first actuator 506 protrudes through a first actuator opening 516 of first handle half 502, and second actuator 562 protrudes through a second actuator opening 566 of first handle half 502.

As will be apparent to those skilled in the art, all of the components of handle 500 may be constructed of materials and using methods so that it would be practical for handle 500 to be either single patient use disposable or reusable after sterilization in a steam autoclave such as used in hospitals.

Figure 4:
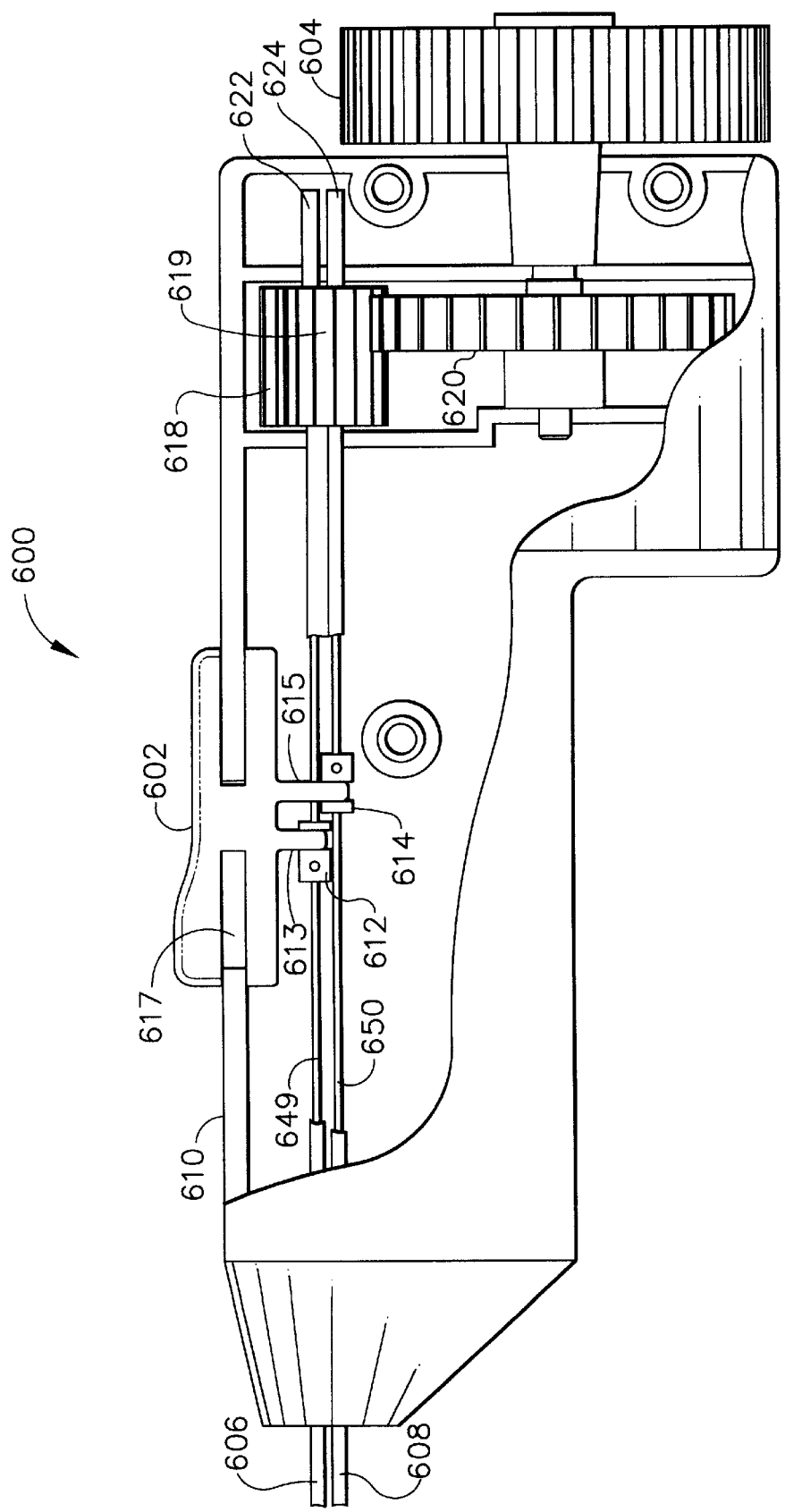
FIG. 4 is a side view of a drive unit 600 shown in FIG. 1, with a portion of drive unit shell 610 removed to reveal the internal components.

FIG. 4 is a side view of drive unit or needle driver 600 with a portion of a drive unit shell 610 removed to reveal the internal components. Third actuator 602 has a first extension 613 for engaging a first connector 612, which is fixedly attached to right shaft 649 of right drive cable 606. Third actuator 602 has a second extension 615 for engaging a second connector 614, which is fixedly attached to left shaft 650 of left drive cable 608. An operator may slide third actuator 602 in either longitudinal direction in a translation slot 617 of drive unit shell 610. When an operator slides third actuator 602 in a proximal direction (left), first and second shafts, 649 and 650, translate in the distal (left) direction. When an operator slides actuator 602 in a proximal direction, first and second shafts, 649 and 650, translate in a proximal (right) direction.

Still referring to FIG. 4, fourth actuator 604 of drive unit 600 is rotatably attached to a main gear 620, which meshes with a first shaft gear 618, which in turn meshes with a second shaft gear 619. When an operator rotates fourth actuator 604 in a clockwise direction, first shaft gear 618 rotates in a counter clockwise direction, and second shaft gear 619 rotates in a clockwise direction. As a consequence, right shaft 649 rotates in a counter clockwise direction, and left shaft 650 rotates in a clockwise direction. To simplify operation of drive unit 600, a one way rotation mechanism is preferably included, although not shown in FIG. 4, in drive unit 600 to allow rotation of rotation knob 604 to occur only in the clockwise direction. Such a one way rotation mechanism is disclosed in related patent U.S. Pat. No. 6,015,416. A first shaft drive end 622 has a non-circular cross section and fits slideably into first shaft gear 618, so that right shaft 649 may be rotatably driven by first shaft gear 618, yet be free to translate longitudinally. A second shaft drive end 624 also has a non-circular cross section and fits slideably into second shaft gear 619, so that left shaft 650 may be rotatably driven by second shaft gear 619, yet be free to translate longitudinally.

Those skilled in the art will recognize that drive unit 600 may be made of materials and using methods so that drive unit 600 may be either single patient use disposable or sterilizable in hospitals for multiple patient use.

Figure 5:
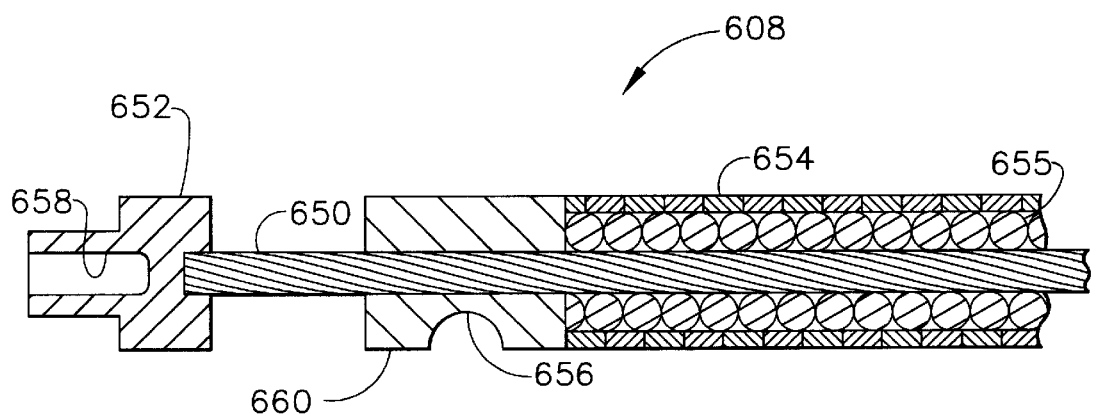
FIG. 5 is a side view in partial section of a left drive cable 608, which operationally engages with drive unit 600 shown in FIG. 1.

FIG. 5 is a side sectional view of the distal portion of left drive cable 608. The distal portion of right drive cable 606 is identical to that of left drive cable 608. Left shaft 650 is attached to a left drive connector 652 having a drive connector bore 658. An inner spring 655, preferably in compression, made of spring wire surrounds left shaft 650 and is covered by a sheath 654, preferably in tension, made of a wire mesh or braided wire. Inner spring 655 and sheath 654 are attached to a ferrule 660 having a pair of ferrule indentations 656 for retention in head assembly 100 (see FIG. 19). Right and left drive cables, 606 and 608, are flexible but have minimal shape memory and do not elongate when tensioned during usage. Preferably, drive cables 606 and 608 have the ability to transmit rotation or translation were without kinking or elongation. A particularly suitable sheathed cable for right and left drive cables, 606 and 608, is a flexible camera cable for a remote shutter actuator, available from Brandess-Kalp Aetna Group, 701 Corporate Woods Parkway, Vernon Hills, N.J. 60061.

Figure 6:
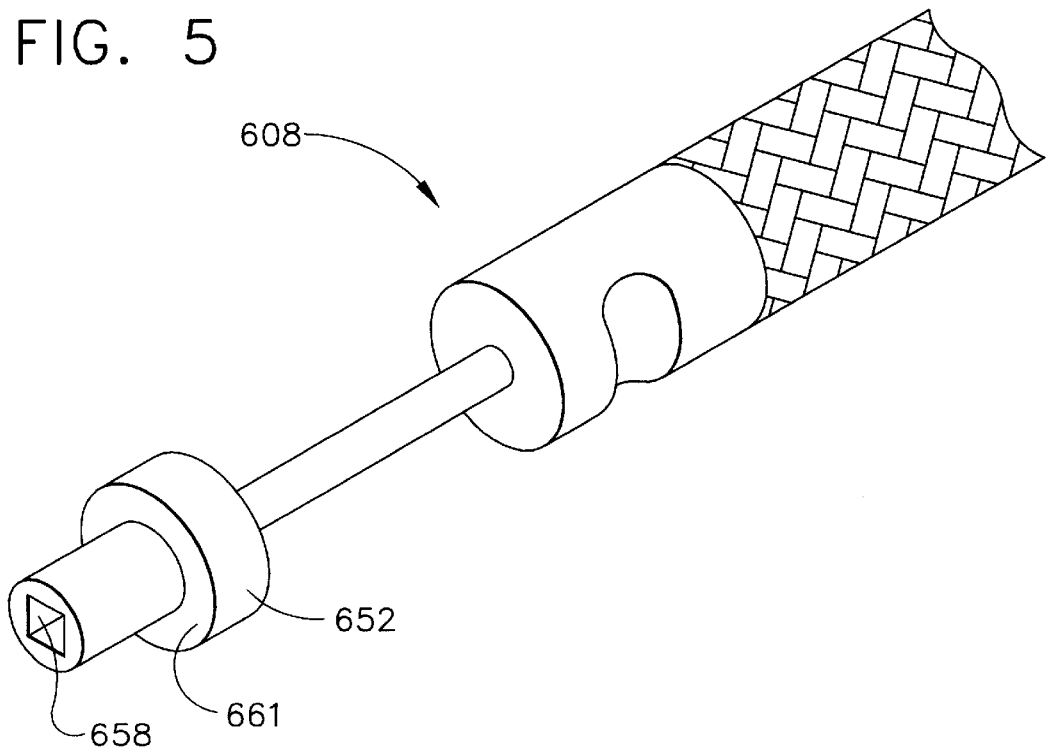
FIG. 6 is an isometric view of left drive cable 608 shown in FIG. 5.

FIG. 6 is an isometric view of the distal portion of left drive cable 608 shown in FIG. 5. In this view it can be seen that connector bore 658 is non-circular so that left drive cable 608 can transmit a rotational force from drive unit 600 to head assembly 100 shown in FIG. 3. A pushing surface 661 on left drive connector 652 permits left drive cable 608 to transmit a translational force from drive unit 600 in the distal direction to head assembly 100. Right drive cable 606 (see FIG. 4) is configured similarly also to transmit rotational and translational forces from drive unit 600 to head assembly 100.

Figure 7:
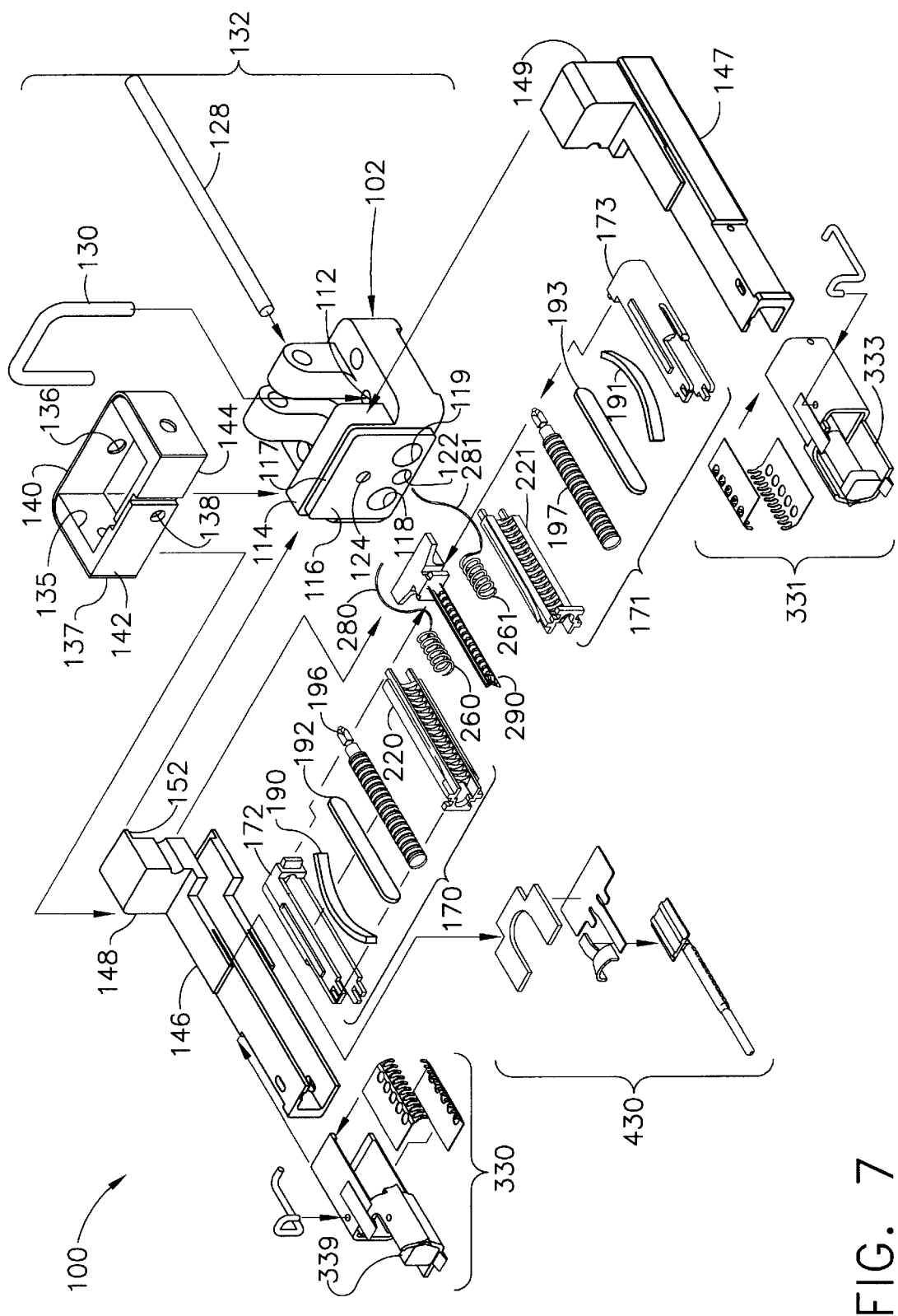
FIG. 7 is an exploded isometric view of head assembly 100 shown in FIG. 1.

FIG. 7 is an exploded, isometric view of several components of the working end (tissue contacting portion) of the present invention and generally includes head assembly 100 and block assembly 132. Head assembly 100 further includes an upper pin assembly 430, a right tissue holder 330 having a right needle receiver 339, a left tissue holder 331 having a left needle receiver 333, a right roller assembly 170, a left roller assembly 171, a plow 290, a right frame 146, and a left frame 147. Right roller assembly 170 further includes a right roller housing 172, a right leaf spring 190, a right roller plate 192, a right roller 196 (having a plurality of annular rings disposed thereon), a right needle guide 220 and right helical needle 260 having a right suture 280 attached to it. Left roller assembly 171 further includes a left roller housing 173, a left leaf spring 191, a left roller plate 193, a left roller 197 (having a plurality of annular rings disposed thereon), a left needle guide 221, and a left helical needle 261 having a left suture 281 attached to it. Right and left sutures, 280 and 281, are preferably made from a polypropylene monofilament, size 7-0(0.003 in.), as is typically used for sewing together blood vessels for a coronary artery bypass graft procedure. The above assembly being one example of a means for two hollow organs about a passageway therebetween. The remaining components shown in FIG. 7 are preferably made from stainless steel using numerous well-known manufacturing techniques including injection molding of stainless steel.

Still referring to FIG. 7, block assembly 132 includes a block 102 generally for mounting head assembly 100 to handle 500 as shown in FIG. 3. Block 102 has a support wall 114 having a support face 116 configured for aligning and supporting left and right frames, 147 and 146, of head assembly 100. A right frame ledge 152 on a right turret 148 of right frame 146 fits closely onto a support face edge 117 of support face 116. A left turret 149 of left frame 147 also fits closely onto support face edge 117. Support face 116 has a right roller hole 118, which provides access for right drive cable 606 (not shown) to connect to right roller 196. A left roller hole 119 similarly provides access for left drive cable 608 (not shown) to connect to left roller 197. Support face 116 has a smaller, central hole 122 for left and right sutures, 280 and 281, to exit head assembly 100. An assembly pin hole 124 in support face 116 retains a clamp pin 128.

Figure 27:
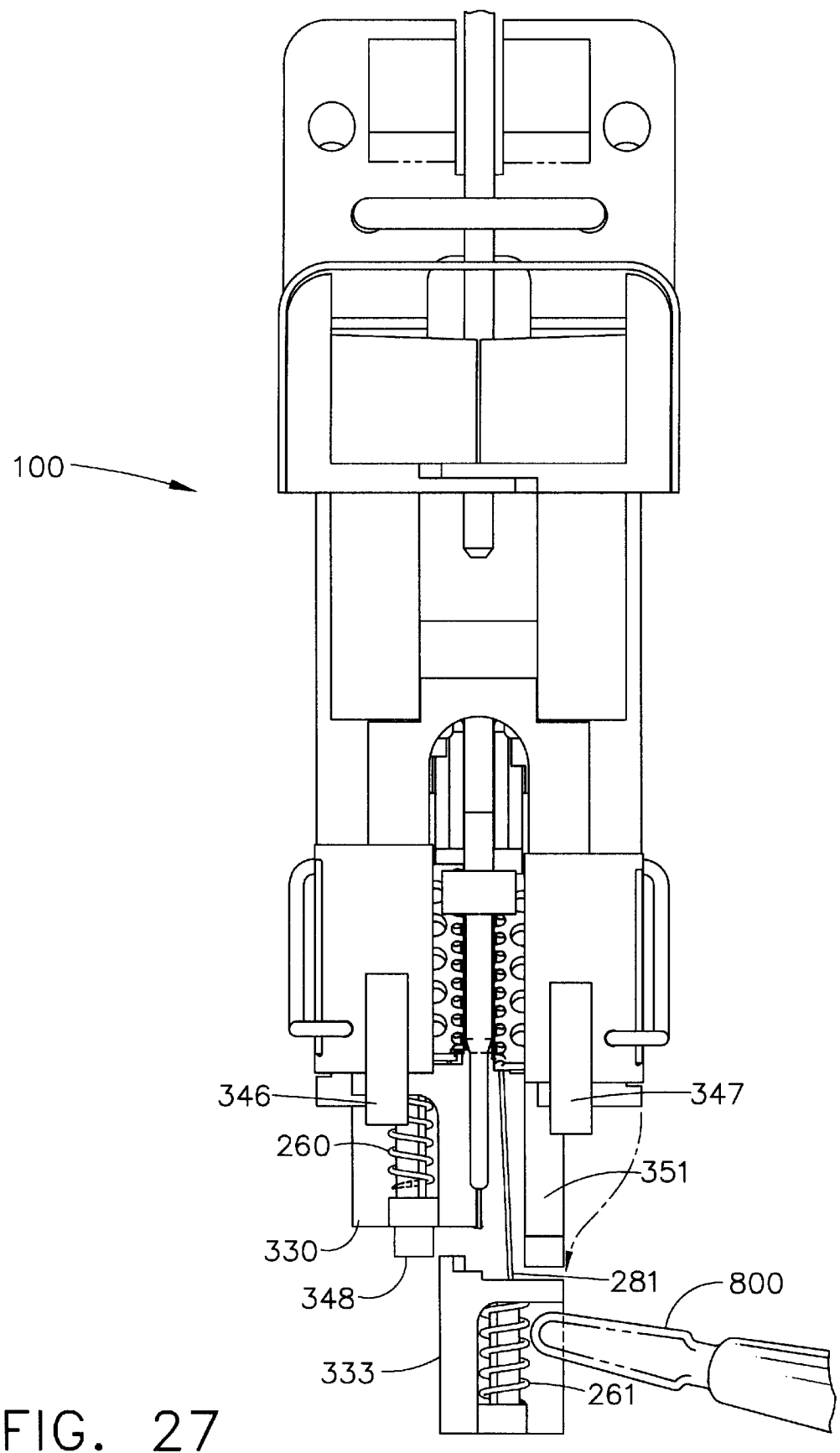
FIG. 27 is a top view of head assembly 100 and is shown with a surgical tool 800 removing a left needle receiver 333 containing left helical needle 261.
Figure 28:
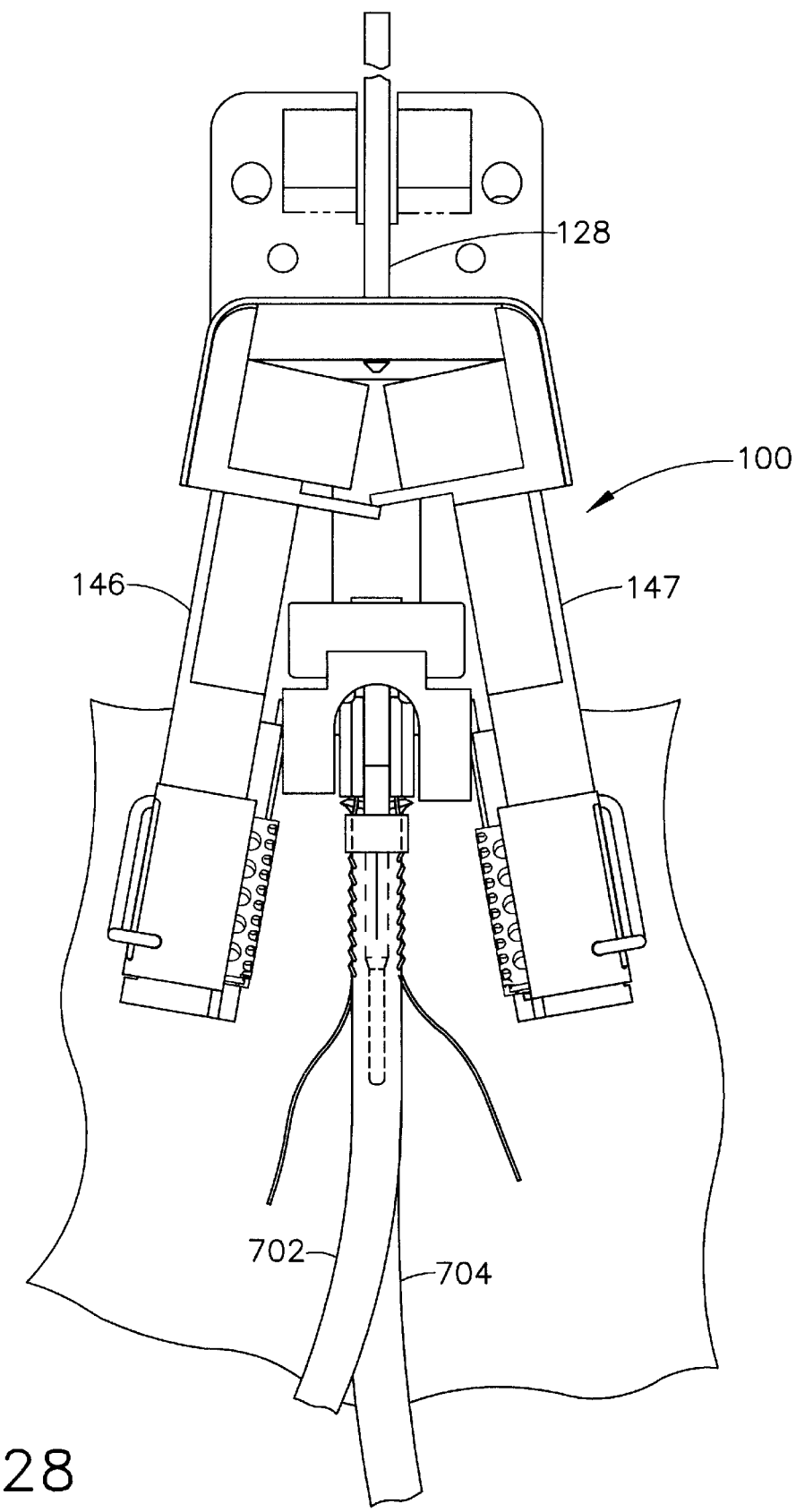
FIG. 28 is a top view of head assembly 100 with a right head frame 146 and a left head frame 147 shown in an open position for removing head assembly 100 from first vessel 702 and second vessel 704.

FIG. 7 also shows a clamp 137 of block assembly 132 having a clamp opening 135, which fits over right and left turrets, 148 and 149, of right and left frames, 146 and 147. Clamp 137 comprises a right clamp element 142 and a left clamp element 144 attached to a clamp spring 140, preferably by welding, so that right and left clamp elements, 142 and 144, are normally sprung apart in an open position. Right turret 148 is attached, preferably by welding, to right clamp element 142. Left turret 149 is attached, preferably by welding, to left clamp element 144. When clamp 137 is normally sprung apart, right frame 146 and left frame 147 are sprung apart in a vee-shaped configuration as shown in FIG. 28. A right clamp element hole 138 in right clamp element 142 aligns with a left clamp element hole (not visible) in left clamp element 144 when clamp 137 is in a closed position as shown in FIG. 7. Clamp pin 128 assembles through a clamp spring hole 136, right clamp element hole 138, the hidden left clamp element hole in left clamp element 144, and pin assembly hole 124 in block 102, to hold clamp 137 in the closed position. When clamp 137 is held in a closed position, right frame 146 and left frame 147 are held together as shown in FIG. 27.

Clamp 137 in FIG. 7 also includes a U-shaped, retainer wire 130 for insertion into a pair of shaft retention holes 112 (only one shaft retention hole 112 is visible) in block 102. Right and left drive cables, 606 and 608, (not shown in FIG. 7) are retained in block 102 by retainer wire 130.

Figure 19:
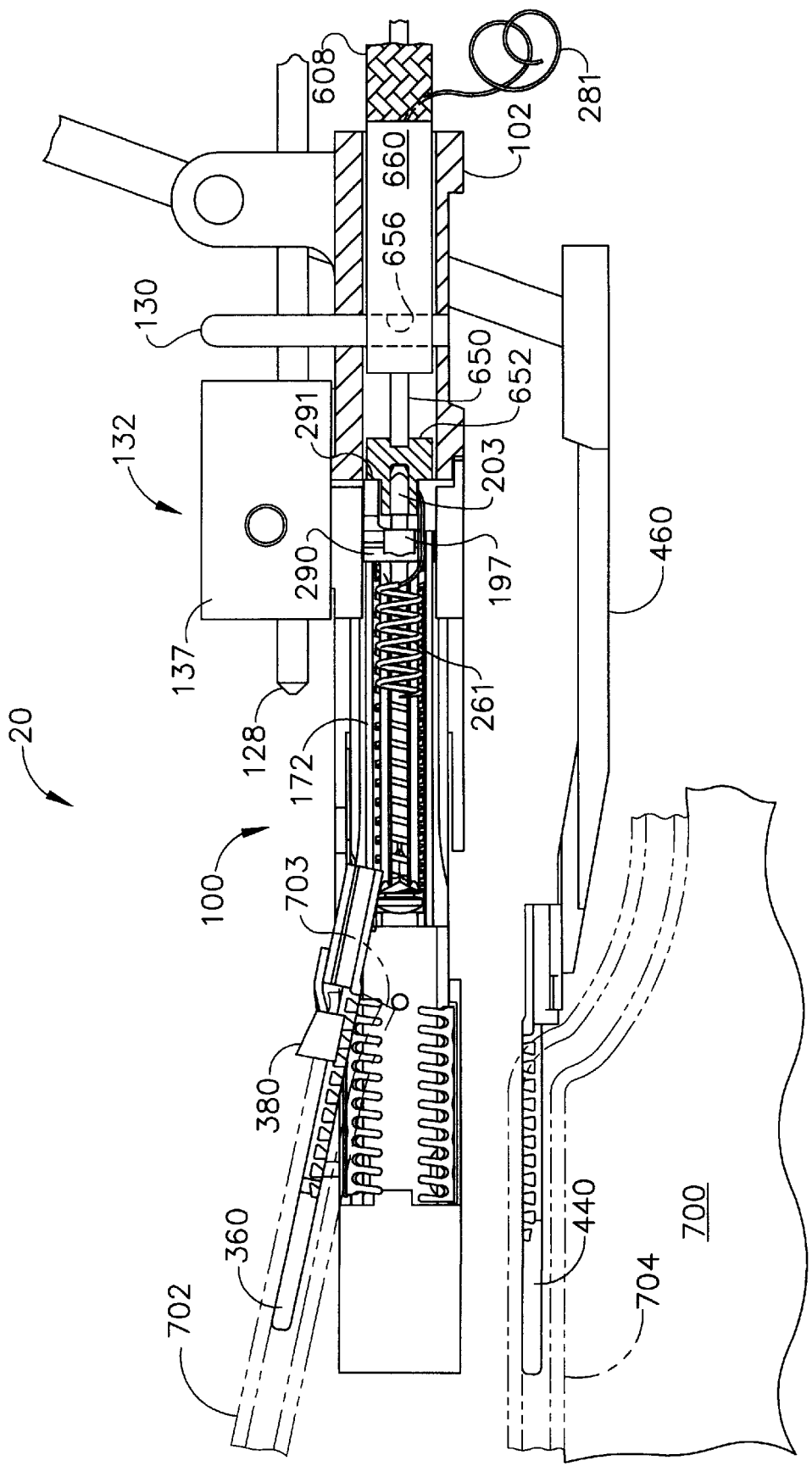
FIG. 19 is a side sectional view of head assembly 100 taken at line 19—19 in FIG. 14, showing an upper tissue pin 360 inserted into a first vessel 702, and a lower tissue pin 440 inserted into a second vessel 704, and with lower pin assembly 460 spaced apart from head assembly 100.

Turning briefly to FIG. 19, a side sectional view of head assembly 100 reveals left drive cable 608 retained in block 102 by retainer wire 130 engaging with ferrule indentation 656 of ferrule 660 of left drive cable 608. Left shaft 650 is shown attached to left shaft connector 652, which is operationally engaged on a left drive post 203 of left roller 197 (partial view) for rotation and translation. Although not visible in FIG. 19, right drive cable 606 is attached in a similar manner to right roller 196 and block 102.

Now referring to FIGS. 8 and 9, in the exploded isometric views, right roller assembly 170 is shown in alignment with plow 290 and left helical needle 261. The following description for the right roller assembly 170 is also descriptive of the left roller assembly, except that left helical needle 261 is driven in the opposite rotational direction of right helical needle 260 in order to counteract the forces during operation within head assembly 100. The primary function of right roller assembly 170 is to align and rotate helical needle 260 in the counter clockwise direction (looking proximal to distal) to drive helical needle 260 through tissue. Each rotation of helical needle 260 constitutes a stitch in the tissue, thus a running stitch may be made by multiple rotations of helical needle 260. Right helical needle 260 comprises a plurality of helical coils 264 and a tip 262 for penetration of tissue. In the free state, helical needle 260 appears circular when viewed from an end. When head assembly 100 is clamped onto tissue, helical needle 260 appears slightly elliptical when viewed from the end because the needle is held tightly between right roller 196 and plow 290 so that the needle may be driven by rotation of right roller 196. Right roller 196 comprises a plurality of annular grooves 198 spaced evenly apart. A right drive post 202 extends from the proximal end of right roller 196 for operational engagement with right drive cable 606 (not shown). Right drive post 202 has a non-circular cross section for rotational engagement, and a tapered tip 204 for easy assembly. Right needle guide 220 has a plurality of ribs 222 spaced evenly apart approximately the same distance as the helical coils 264 on right helical needle 260. Each individual helical coil 264 projects between two adjacent ribs 222 so as to contact the inside of the corresponding one of a plurality of annular grooves 198 in right roller 196. Right roller 196 is forcibly held against helical needle 260 by leaf spring 190 sandwiched between right roller housing 172 and right roller plate 192, which bears against right roller 196. FIG. 8 shows the free state of right leaf spring 190, and FIG. 9 shows the assembled, compressed state of right leaf spring 190. A shank 200 on right roller 196 rotates in a half-bushing 188 on right roller housing 172. A roller end 206 is retained against the inside of a retaining arm 224 of right needle guide 220. Retaining arm 224 inserts into a retention slot 180 and a retention hole 182 of right roller housing 172. Right needle guide 220 further includes a guide ramp 226 and guide slot 227, which are instrumental in moving the upper pin assembly 430 (see FIG. 7) during operation as will be described. Similarly, right needle guide 220 includes a lower guide ramp 242 and a lower guide slot 244, which are instrumental in holding the lower pin assembly 460 (see FIG. 3) during operation, as will be described later.

Figure 10:
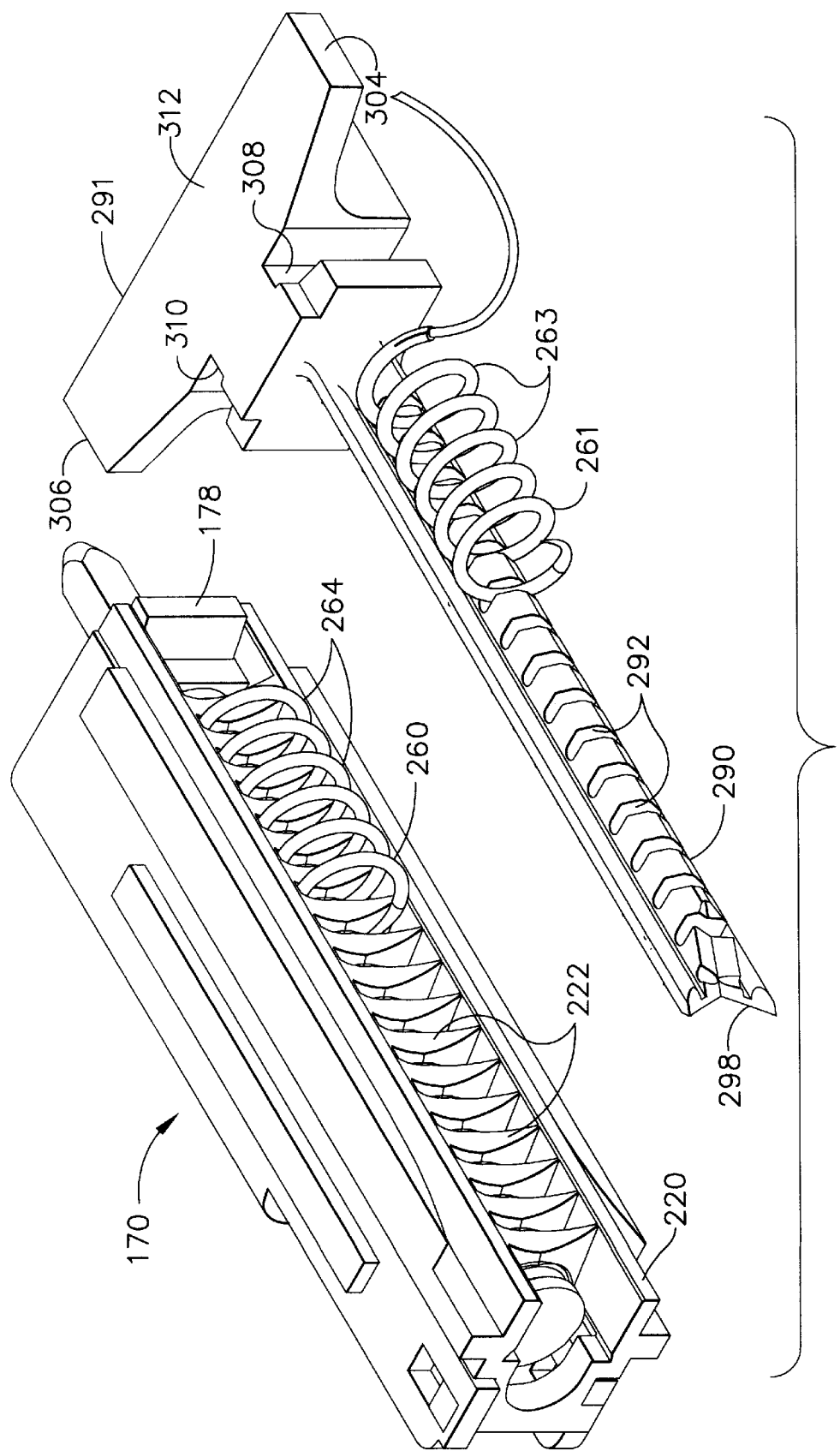
FIG. 10 is an isometric view of right roller assembly 170 shown with a plow 290 and a left helical needle 261.

FIG. 10 is an isometric view of right roller assembly 170 containing right helical needle 260 in a start position, plow 290, and left helical needle 261, also in a start position. Plow 290, which is a means for incising at least one of the hollow organs so as to create a passageway therebetween, includes a plurality of left plow grooves 292 spaced evenly apart about the same distance as ribs 222 on right needle guide 220. A plurality of left helical coils 263 are positioned in a like plurality of left plow grooves 292. Similarly, a plurality of right helical coils 264 are positioned in a like plurality of right plow grooves (not visible). A plow blade 298 on the distal end of plow 290 is adapted to cut and separate tissue as plow 290 is translated longitudinally in the distal direction. Plow 290 includes a carriage 312 having a right wing 306 and a left wing 304. When an operator actuates third actuator 602 (see FIG. 4) to translate right and left drive cables, 606 and 608, in the distal direction, right cable pushing surface 660 (see FIG. 6) of right drive cable 606 pushes against carriage edge 291 of right wing 306 of carriage 312. Similarly, a left cable pushing surface (not shown) pushes against carriage edge 291 of left wing 304. A right housing lip 178 assembles into a right wing notch 310 of carriage 312. A left housing lip (not shown) assembles into a left wing notch 308. When carriage 312 is pushed by right and left drive cables, 606 and 608, carriage 312 of plow 290 in turn pushes right roller assembly 170 and left roller assembly 171 (FIG. 7) in the distal direction. This moves right roller housing 172 (FIG. 7) and left roller housing 173 (FIG. 7) from an initial position to an operational position for joining the hollow organs together.

FIG. 11 is an exploded, isometric view of right tissue holder 330. Left tissue holder 331 (see FIG. 7) is a mirror image of right tissue holder 330. Right tissue holder 330 comprises a channel 349, and the following elements, which are attached to channel 349, preferably by welding: an right upper spring latch 346, a right lower spring latch 348, an right upper tissue clamp 332, and a right lower tissue clamp 334. Upper tissue clamp 332 locates into an upper channel recess 350 and has a plurality of upper clamp flutes 354. Lower tissue clamp 334 locates into a lower channel recess 352 and has a plurality of lower clamp flutes 356. A wireform connector 336 inserts into channel hole 358 and a right frame hole hidden from view in FIG. 11, and removably attaches channel 349 to right housing 146. Right tissue holder 330 further comprises right needle receiver 339, which includes a needle receiver bracket 338 and a needle holder 340. Needle holder 340 includes a right post 342 and a head 341, which is attached, preferably by welding, to needle receiver bracket 338. Right needle receiver 339 is removably retained in right tissue holder 330 by upper spring latch 346 engaging a bracket arm 344 of needle receiver bracket 338, and lower spring latch 348 engaging a bracket edge 343 of needle receiver bracket 338, so that post 342 of needle receiver 339 is in the path of right helical needle 260 as shown in FIGS. 12 and 13.

FIG. 12 shows the alignment for assembly of right tissue holder 330 and right roller assembly 170 to right frame 146. (Left tissue holder 331 and left roller assembly 171 assemble to left frame 147 in the identical manner.) A housing rail 174 on right roller housing 172 slides into a frame slot 151 of right frame 146, permitting right roller housing 170 to move freely along shelf 156 of right frame 146. In FIG. 13, right roller housing 170 is positioned in the initial position, which is the most proximal position, and retained in right frame 146 by attaching right tissue holder 330 to right frame 146 by wireform 336 into elongated hole 150, channel hole 358, and the hole hidden from view on right frame 146. Right frame 146 includes an upper tissue pin slot 160 and a lower tissue pin slot 158, which force upper pin assembly from the up position to the low position as will be described later.

Figure 14:
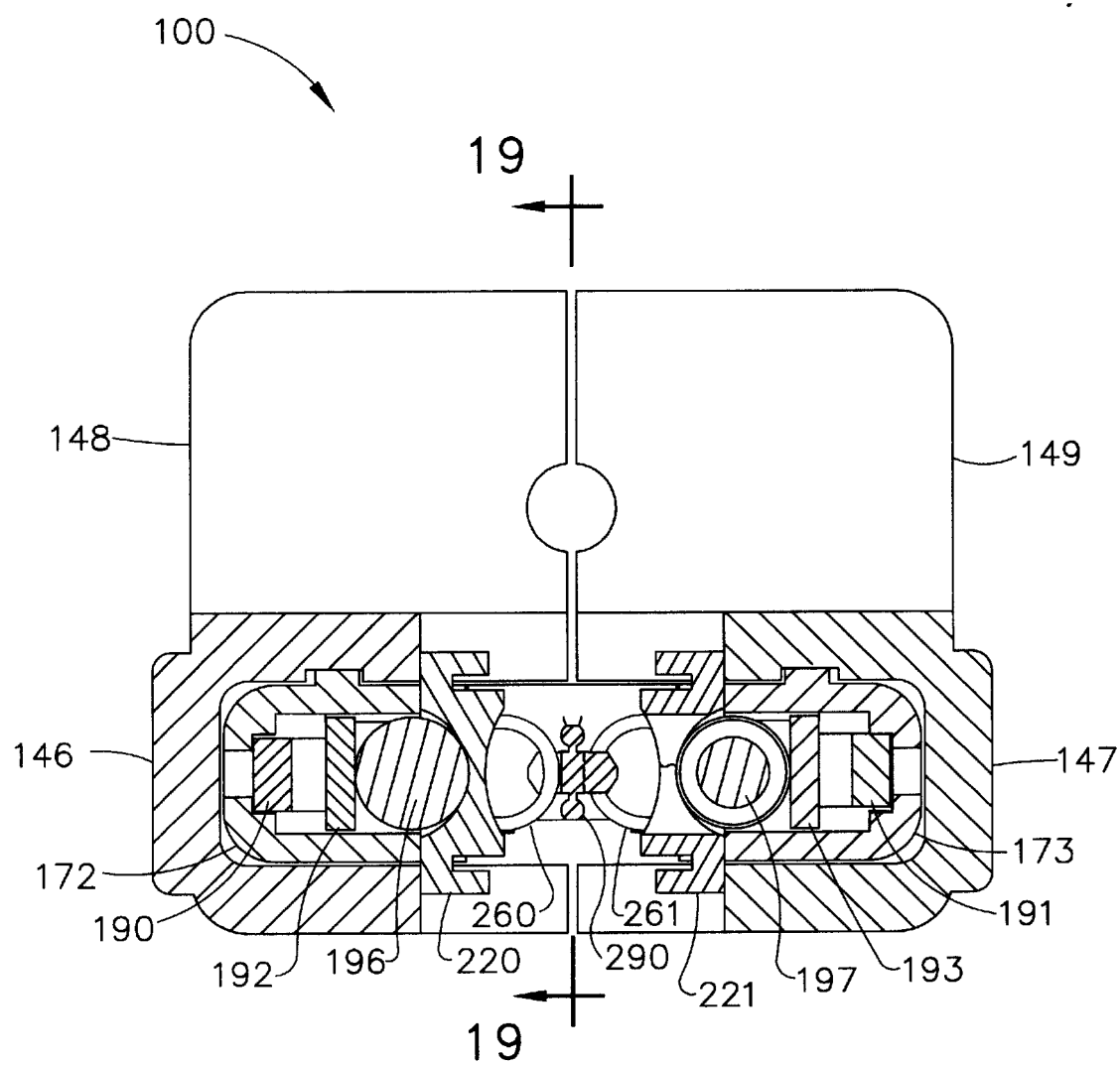
FIG. 14 is a cross-sectional view of head assembly 100 taken through line 14—14 in FIG. 2.

FIG. 14 is a cross sectional view, taken along line 14—14 of FIG. 2, of head assembly 100. Right frame 146 and left frame 147 are shown held together in the closed position. Plow 290 is shown in the center and is engaged with right helical needle 260 and left helical needle 261. Right and left helical needles, 260 and 261, are shown to be out of phase. That is, right helical needle 260 is slightly more distal in the longitudinal direction than left helical needle 261. The right and left roller assemblies, 170 and 171 (see FIG. 10), are offset longitudinally by half the distance between ribs 222 on needle guide 220, and anvil 290 is configured to match this offset, so that stitches created on the right side of the hollow organs joined together are not directly opposed by stitches on the left side. Also shown in cross section in FIG. 14 are the following: right and left roller housings, 172 and 173; right and left leaf springs, 190 and 191, right and left roller plates, 192 and 193; right and left rollers, 196 and 197; and right and left needle guides, 220 and 221. Right turret 148 of right frame 146 and left turret 149 of left frame 147 are shown together as they would be held by clamp 147 (not shown) as described for FIG. 7.

FIG. 15 is an exploded isometric view of upper pin assembly 430, which comprises an upper tissue pin 360, a spring plate 400, a guide plate 420, and a tissue holder 380, all of which are preferably made of a stainless steel. Upper tissue pin 360 includes a pin platform 368 at its distal end having a right flange 366, a left flange 365, a right ridge 405, a left ridge 406, and a central flat 367. Upper tissue pin 360 further includes a plurality of upper pin slots 361 on a middle region 359, an insertion region 362, a pin tip or distal end 363, and an upper pin channel 364 running longitudinally through the entire length of upper tissue pin 360. Spring plate 400 includes a bridge 404, a right and a left spring stop, 403 and 401, extending from one side of bridge 404, and a spring arm 402 extending from the same side of bridge 404 and between right and left spring stops, 403 and 401. Spring arm 402 is attached, preferably by welding, to flat 367 of platform 368 of tissue pin 360, and is spring biased to be in a normally up position as shown in FIG. 19. Right and left spring stops, 403 and 401, hit upon right and left ridges, 405 and 406, to limit the upper position of tissue pin 360. Tissue holder 380 comprises a holder arm 381 and a cuff 382. Holder arm 381 attaches, preferably by welding, to spring arm 402. Cuff 382 assists in holding the open end of one of the hollow organs to be anastomosed during the sequence of operation, as will be described later. Guide plate 420 comprises a guide plate extension 424, which is attached, preferably by welding, to bridge 404 of spring plate 400. Guide plate 420 further comprises a cut-out 422 to provide clearance for tissue pin 360 to move to the up position. FIG. 16 is an isometric view of the assembled upper tissue pin 430, shown as the tissue pin 360 would be oriented when in a down position.

Figure 17:
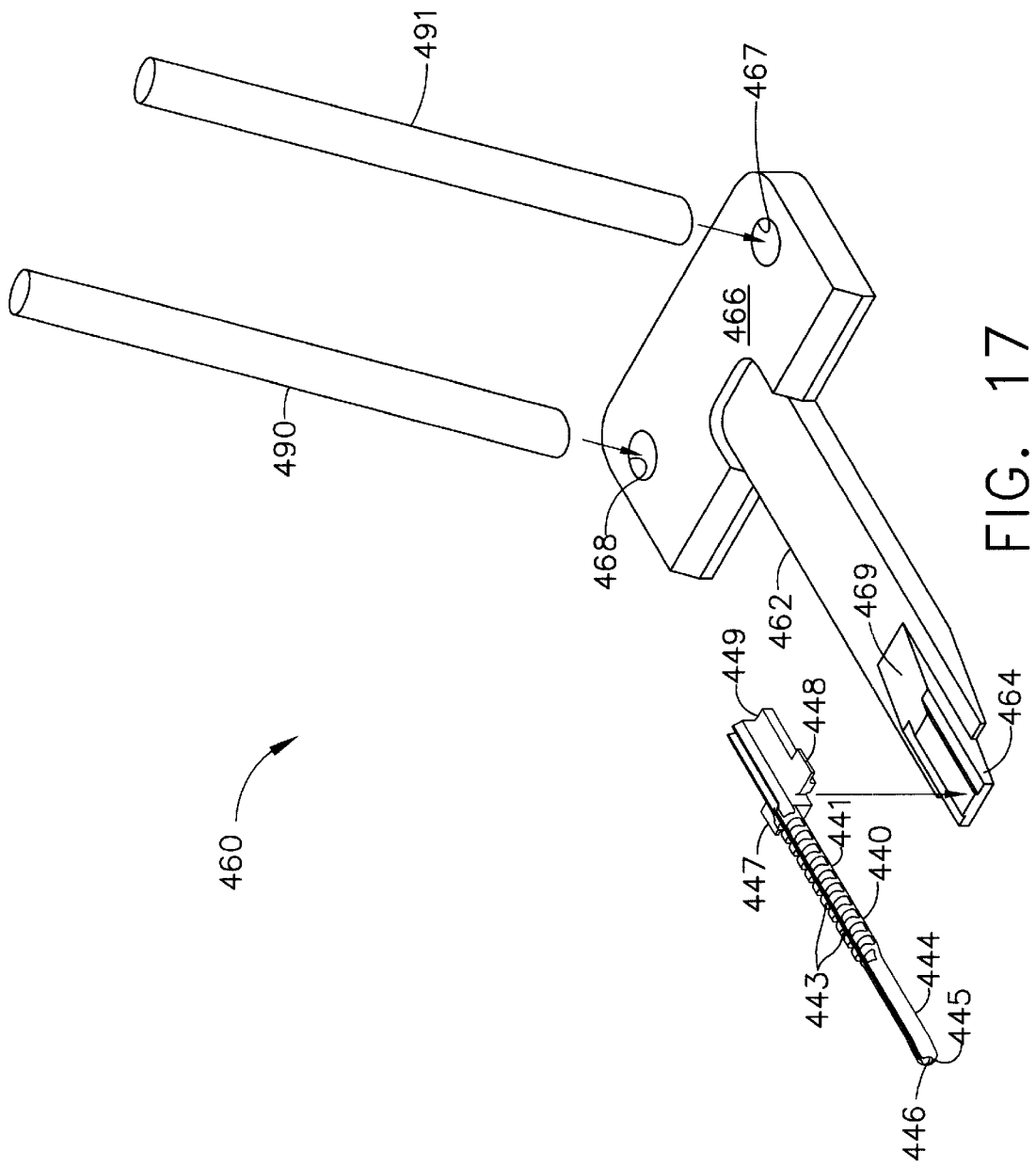
FIG. 17 is an exploded isometric view of a lower pin assembly 460.
Figure 18:
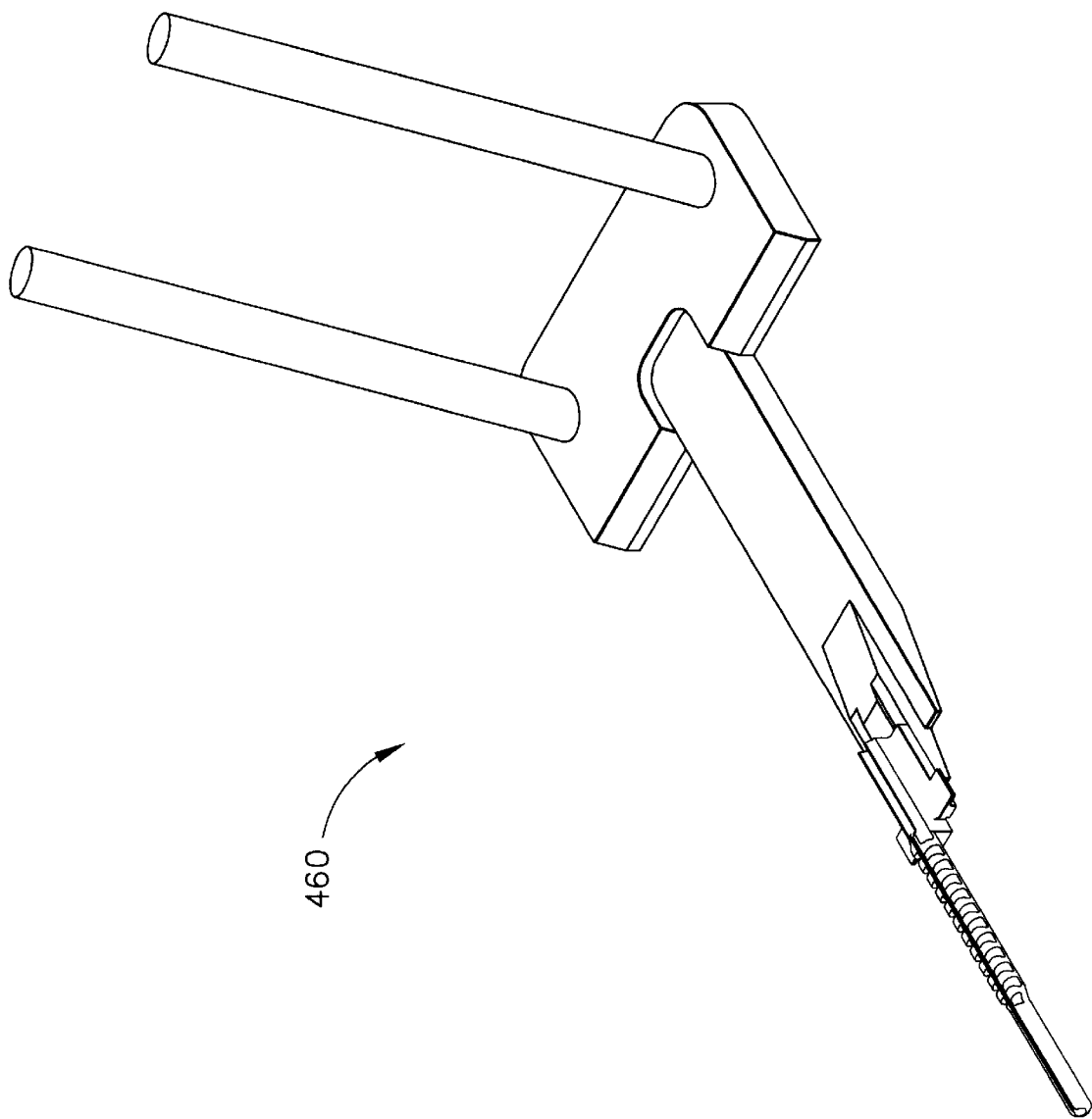
FIG. 18 is an isometric view of assembled, lower pin assembly 460 shown in FIG. 17.

FIG. 17 is an isometric view of lower pin assembly 460, which comprises a lower tissue pin 440, a pin support 466, right rail 490, and left rail 491, all of which are preferably made from stainless steel. Right rail 490 inserts into right rail hole 468 and is preferably welded together. Left rail 491 inserts into left rail hole 467 and is also preferably welded together. Pin support 466 includes a support arm 462 having a support arm ramp 469 and a support extension 464. Lower pin 440 comprises a lower pin base or proximal end 449, which is attached, preferably by welding, to support extension 464. A right finger 447 and a left finger 448 extend from the sides of lower pin base 449. Lower pin 440 further comprises a plurality of lower pin slots 443 on a lower pin middle region 441, an lower pin insertion region 444, a lower pin tip or distal end 445, and a lower pin channel 446 extending through the length of lower pin 440. FIG. 18 is an isometric view of the lower pin assembly 460 shown in FIG. 17.

FIGS. 19–28 show various steps of the operational sequence for the present invention. FIG. 19 is a side view of working portion 20 (see FIG. 2) of the present invention, but with left frame 147 and left roller assembly 171 (except for left helical needle 261) removed. Head assembly 100 is shown in the first position spaced apart from lower tissue pin assembly 460. Upper tissue pin 360 is shown in the up position and inclined relative to the longitudinal axis of head assembly 100. Although not apparent in FIG. 19, head assembly 100 is in the closed position (a top view of head assembly 100 is also shown in the closed position in FIG. 26). Right roller housing 172 is in the initial (furthest to the right) position. Left helical needle 261 is shown in the start (furthest to the right) position. A first vessel 702, also referred to as a first hollow organ, is shown in phantom view positioned onto upper tissue pin 360. First vessel 702 may, for example, be a harvested vein or artery from the patient. A second vessel 704, also referred to as a second hollow organ, is shown in phantom view positioned onto lower pin assembly 460. As disclosed in U.S. Pat. No. 6,015,416, upper and lower tissue pins, 360 and 440, may be penetrated into the respective vessels after a surgical cutting instrument (not shown) is first used to create a tiny incision in the vessel. Second vessel 704, which may be a stenosed coronary artery, is shown still attached to an organ 700, which may be the heart of a surgical patient. Cuff 380 is shown clasping around the posterior side and near an open end 703 of first vessel 702 to help hold open end 703 during the operational sequence. Left drive cable 608 is shown attached to head assembly 100 by retainer wire 130 engaging with ferrule indentations 656. Left shaft 650, which translates in the distal direction and then rotates in the counter clockwise direction during the operational sequence, is initially stationary for this step. Left drive connector 652, attached to left shaft 650, abuts against carriage edge 291 of plow 290. Left drive connector 652 is also rotationally attached to left drive post 203 of left roller 197. Similarly, right drive cable 606 (hidden behind left drive cable 608) is operationally engaged with plow 290 and right roller 196 (also hidden). Clamp pin 128 is fully engaged with clamp 137 of block assembly 132 and holding together left and right frames, 146 and 147 (see FIG. 26), in the closed position. Left suture 281 is shown trailing behind left needle 261 and exiting through block 102. Right suture 280 (not shown) trails right needle 260 (hidden in this view) and also exits block 102. Both sutures, 280 (not shown in FIG. 19) and 281, extend freely from head assembly 100 during the operational sequence, and are drawn into head assembly 100 as right and left helical needles, 260 (hidden in FIG. 19) and 261, are advanced and penetrated into first and second vessels, 702 and 704.

Figure 20:
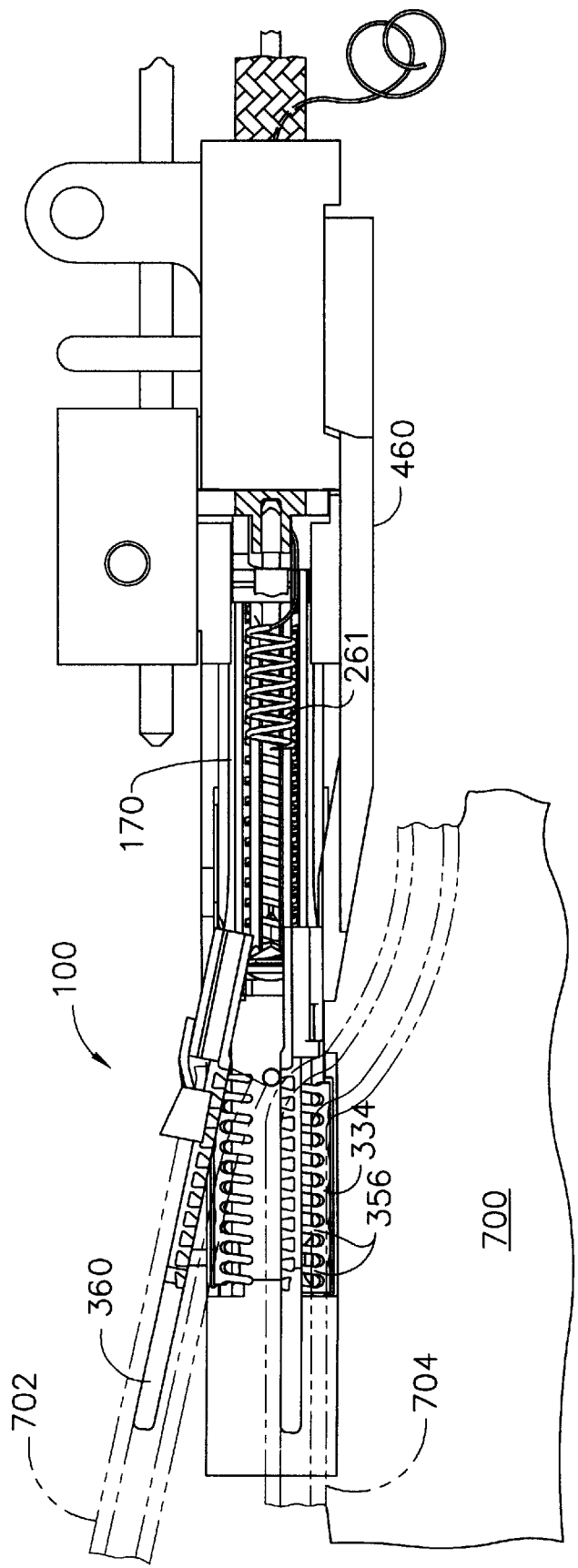
FIG. 20 is the same view as shown in FIG. 19, but with lower pin assembly 460 spaced near head assembly 100.

FIG. 20 is a similar view as FIG. 19 showing the next step in the operational sequence. Head assembly 100 is lowered into the second position so that lower pin assembly 460 and a portion of second vessel 704 are aligned within head assembly 100. Lower clamp flutes 356 of lower clamp 334 press against the sides of second vessel 704. Second vessel 704 is now held directly in the path of right and left helical needles, 260 (hidden) and 261. Second vessel 704 is normally attached to organ 700, and is relatively immobile. Therefore, the operator lowers head assembly 100 close to organ 700 by actuation of first actuator 506 (not shown) as described earlier for FIG. 2. Upper tissue pin 360 and first vessel 702 remain in the up position. First and second helical needles, 260 (hidden) and 261, remain in the start position. Right roller assembly 170 remains in the initial position.

Figure 21:
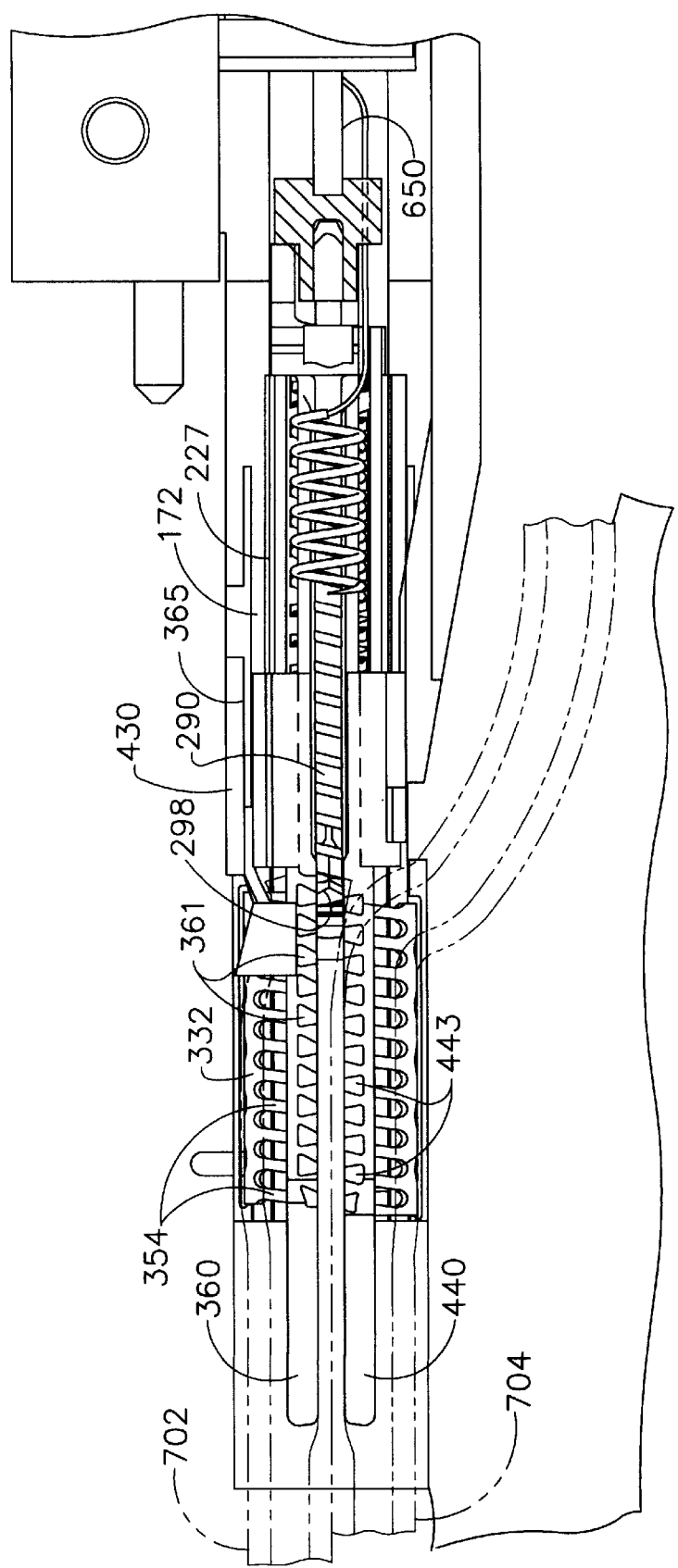
FIG. 21 is the same view as FIG. 20, but with an upper pin assembly 430 adjusted so that first vessel 702 is approximately parallel and close to second vessel 704.

FIG. 21 is a similar view as FIG. 20 showing the next step of the operational sequence. Plow 290 is now shown moved from a proximal position (as shown in FIG. 20) to an intermediate position. Plow blade 298 of plow 290 is immediately proximal to first and second vessels, 702 and 704. The operator moves plow 290 to the intermediate position by the initial actuation of third actuator 602 (not shown) on drive unit 600 as described for FIG. 4, causing right and left shafts, 649 (hidden) and 650, to translate in the distal (left) direction. As already described, translation of right and left shafts, 649 and 650, advances right and left roller assemblies, 170 and 171(not shown), from the initial position to a middle position, still proximal to first and second vessels, 702 and 704. As described for FIG. 8, right roller housing 172 has guide ramp 226 and guide slot 227, and left roller housing 173 (not shown in FIG. 21, see FIG. 7) has a similar ramp and guide slot. As right and left roller housings, 172 and 173 (not shown in FIG. 21) advance to the middle position, right and left flanges, 366 (hidden) and 365, of upper pin assembly 430 (more clearly depicted in FIG. 15), are captured in guide ramp 226 (hidden), then guide slot 227 of right roller housing 172, and simultaneously in the guide ramp and slot of left roller housing 173, causing upper pin assembly 430 to move to the down position. Operation of actuator 602 causes the distal ends 363 and 445 adjacent to one another. Consequently, upper tissue pin 360 and first vessel 702 are moved into the down position within head assembly 100 so that first vessel 702 is aligned parallel and tightly against second vessel 704, and in the path of right and left helical needles, 260 (hidden) and 261. Upper clamp flutes 354 of upper clamp 332 push against first vessel 702 to hold it in place. Plurality of upper pin slots 361 of upper tissue pin 360 are aligned with plurality of lower pin slots 443 of lower tissue pin 440, thus becoming guides within the lumens of first and second vessels, 702 and 704, for first and second helical needles, 260 and 261.

Figure 22:
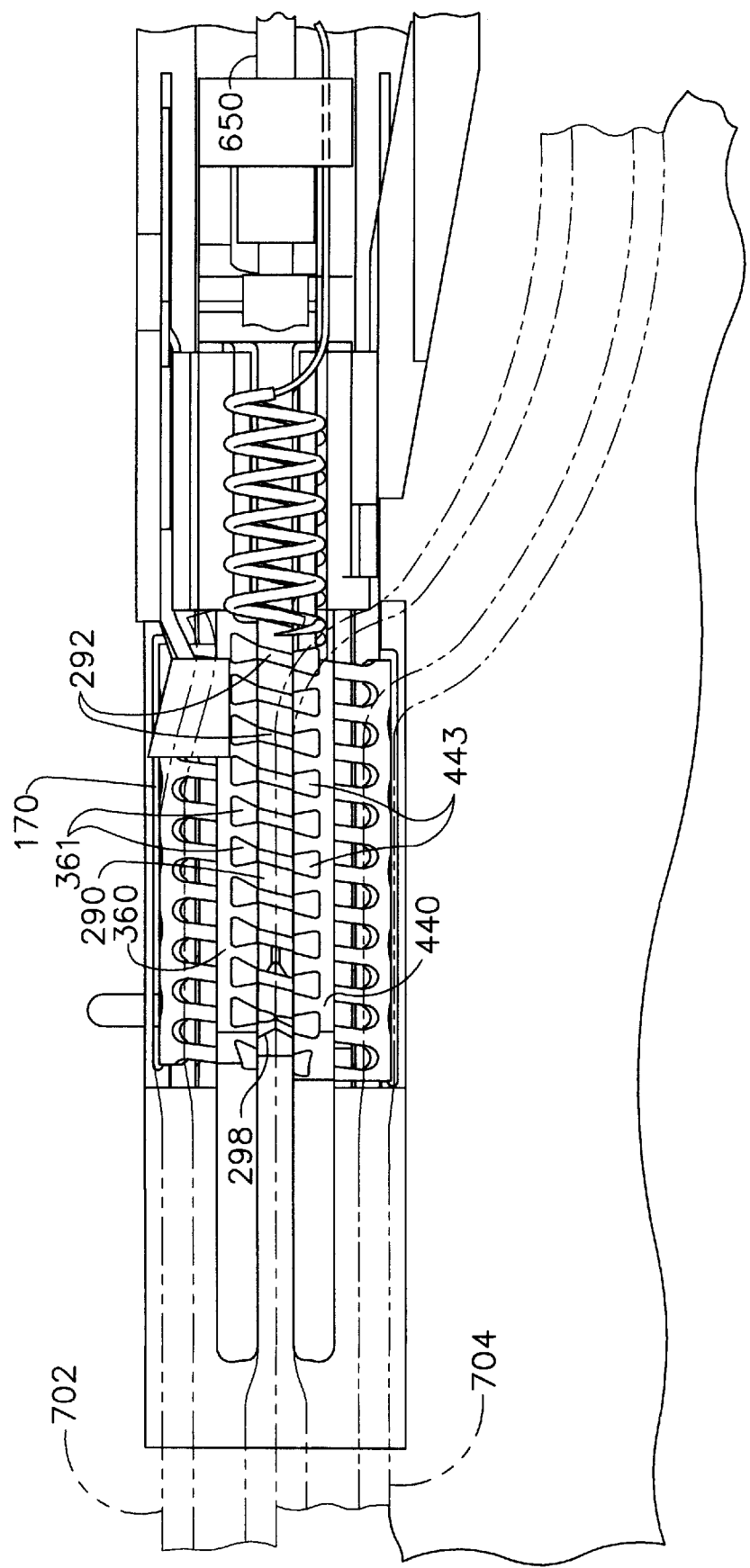
FIG. 22 is the same view as FIG. 21, but with a plow blade 298 shown advanced through first vessel 702 and second vessel 704.

FIG. 22 is a similar view as FIG. 21, showing the next step of the operational sequence. The operator completely actuates third actuator 602 (not shown) on drive unit 600 as described for FIG. 4, thus causing first and second shafts, 649 (hidden) and 650, to translate further in the distal (left) direction). As a result, plow 290 advances to a distal position and plow blade 298 cuts a passageway between first and second vessels, 702 and 704. As plow 290 advances it pushes right and left roller assemblies, 170 and 171 (not shown), to an operational position alongside of first and second vessels, 702 and 704. Plow grooves 292 of plow 290 align with upper pin slots 361 of upper tissue pin 360 and lower pin slots 443 of lower tissue pin 440, to form a path for right and left helical needles, 260 (hidden) and 261.

Figure 23:
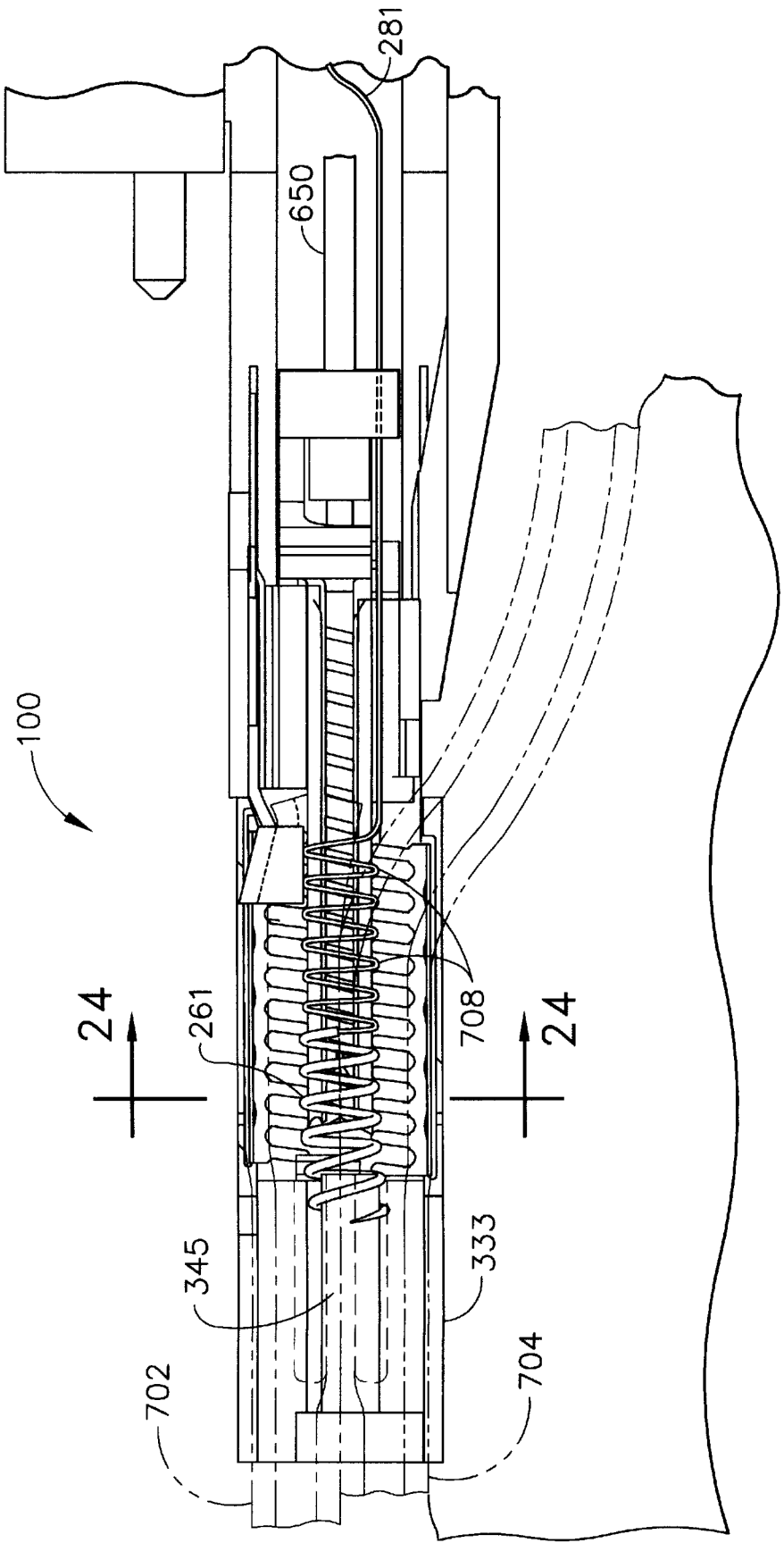
FIG. 23 is the same view as FIG. 22, but with a left helical needle 261 shown rotated through a portion of first vessel 702 and second vessel 704, and with a left suture 281 trailing to create a plurality of left suture stitches 708.

FIG. 23 is similar view as FIG. 22, showing the next step of the operational sequence. The operator actuates fourth actuator 604 (not shown) to rotate first and second shafts, 649 (hidden) and 650, in opposite directions as described for FIG. 4. Right and left helical needles, 260 (hidden) and 261, rotate and advance within head assembly 100 and through first and second vessels, 702 and 704, creating a stitch through them with each full rotation. As a plurality of left suture stitches 708 are completed, left helical needle 261 winds onto a left post 345 of left needle receiver 333. Similarly, right helical needle 260 winds onto right post 342 (hidden) of right needle receiver 330 (hidden), creating a plurality of right suture stitches 706 (hidden in FIG. 23).

Figure 24:
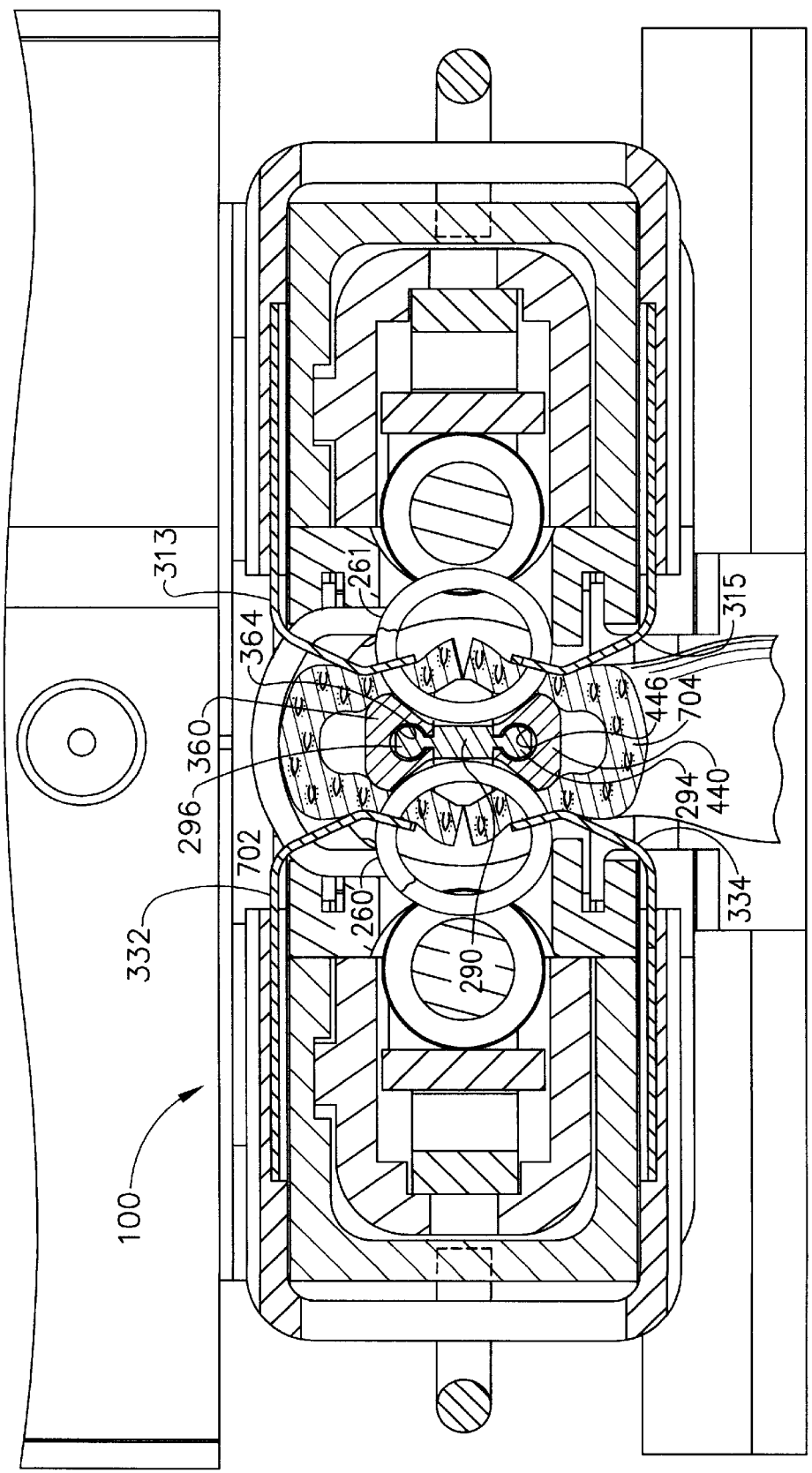
FIG. 24 is a sectional view of head assembly 100 taken at line 24—24 in FIG. 23.

FIG. 24 is a cross-sectional view of head assembly 100 taken along line 24—24 of FIG. 23. Right and left helical needles, 260 and 261, are penetrated through first and second vessels, 702 and 704, which are held tightly by right upper tissue clamp 332, right lower tissue clamp 334, a left upper tissue clamp 313, and a left lower tissue clamp 315. Upper pin channel 364 of upper tissue pin 360 is captured on upper plow rail 296 of plow 290. Lower pin channel 446 of lower pin 440 is captured on lower plow rail 294 of plow 290. The severed edges of first and second vessels, 702 and 704, are partially inverted due to the shape of plow 290. When right and left sutures, 280 and 281, are tied together as will be described for FIG. 30, first and second vessels, 702 and 704, preferably become joined intima-to-intima so that endothelial cells can easily grow over their junction and form a smooth inner lining of the vessels.

Figure 25:
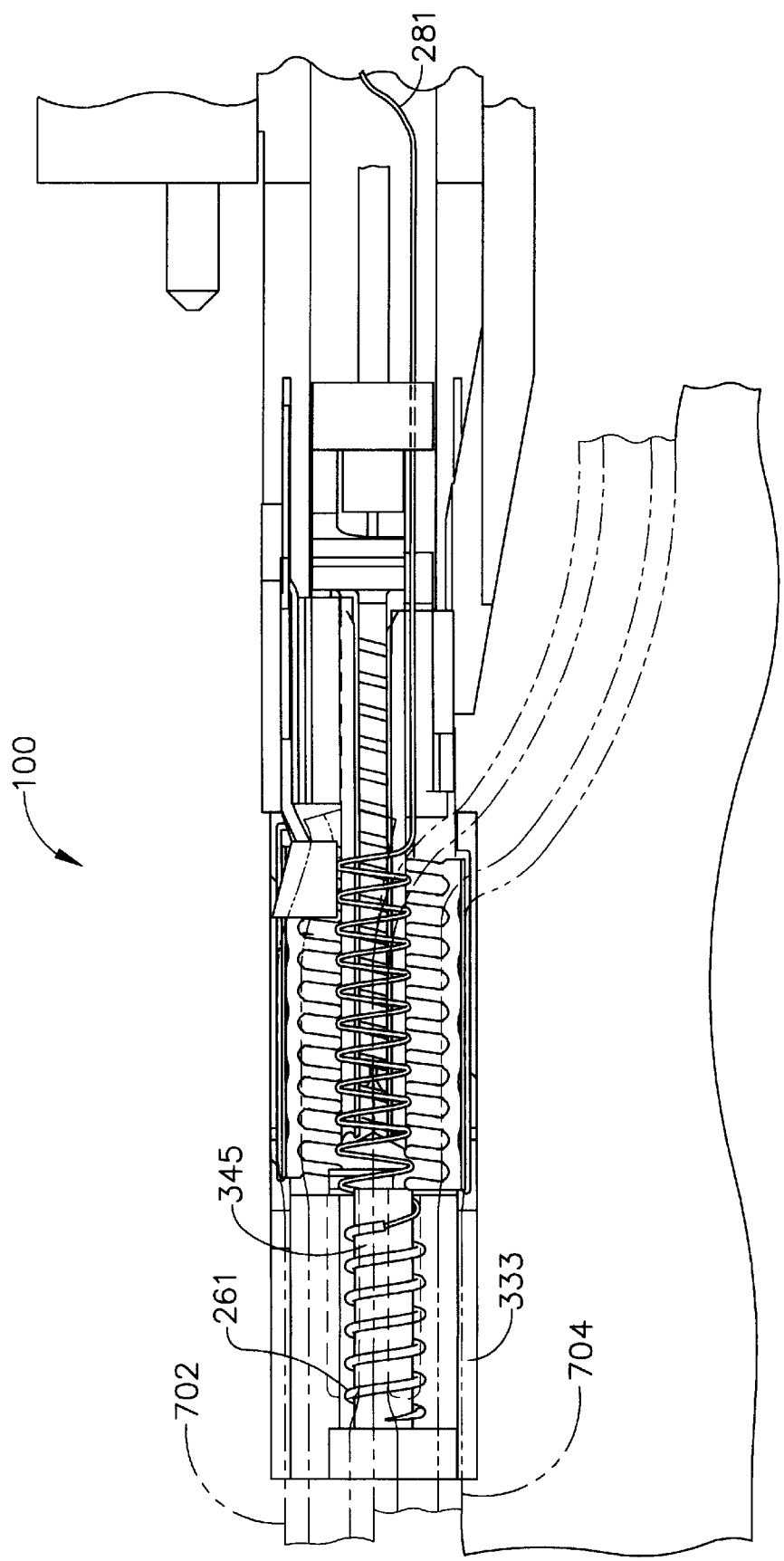
FIG. 25 is the same view as FIG. 23, but with helical needle 261 fully advanced and ready for removal from head assembly 100.

FIG. 25 is similar view as FIG. 23, showing the next step in the operational sequence. Left helical needle 261 is completely wound onto left post 345 of left needle receiver 333. Similarly, right helical needle 260 (hidden) is completely wound onto right post 342 (hidden) of right needle receiver 330 (hidden). Right and left sutures, 260 (hidden) and 281, now join first and second vessels, 702 and 704, together loosely, and will be further tightened manually after head assembly 100 is removed.

Figure 26:
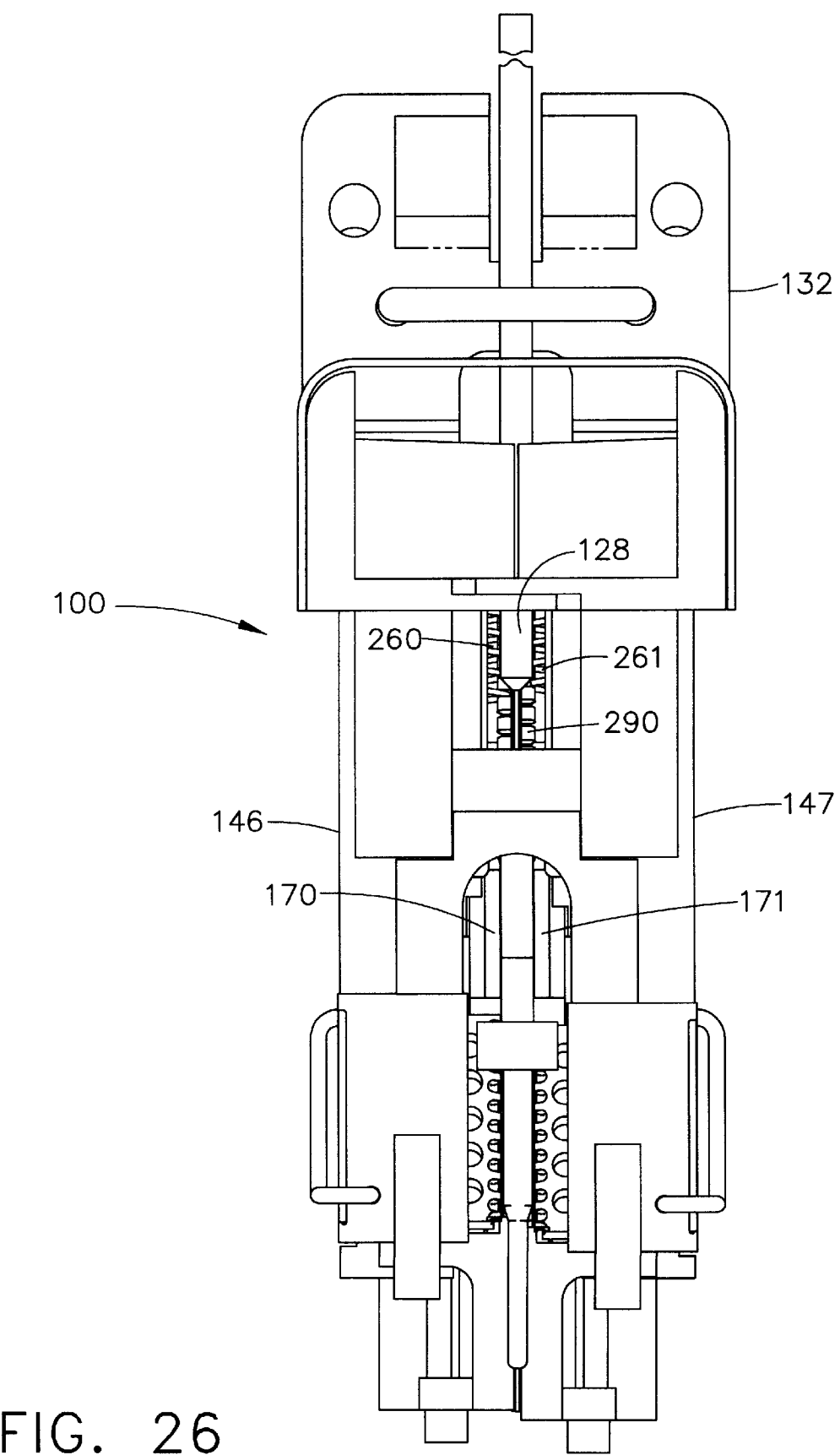
FIG. 26 is a top view of head assembly 100 for when left helical needle 261 is in a start position.

FIG. 26 is a top view of head assembly 100 (shown without first and second vessels, 702 and 704) with right frame 146 and left frame 147 held together in the closed position by clamp pin 128 in block assembly 132. Right and left helical needles, 260 and 261, are partially visible and are in the start position. Plow 290 is partially visible and is in the proximal position. Right roller assembly 170 and left roller assembly 171, are partially visible and are in the initial position.

FIG. 27 is the same view as FIG. 26, showing head assembly 100 (again without first and second vessels, 702 and 704). Left helical needle 261 is completely contained in left needle receiver 333 such as also depicted in FIG. 25. The operator may use a surgical tool 800 to grasp needle receiver 333 and release it from a left upper spring latch 347 and a left lower spring latch 351 of head assembly 100. Left suture 281 is simultaneously drawn through head assembly 100 (and vessels, 702 and 704, if they were contained in head assembly 100). Left helical needle 261 and left needle receiver 333 are cut from left suture 281 using a surgical cutting tool such as a scalpel or scissors. The operator must take care to provide enough free length of suture extending from head assembly 100 for tying a knot later. Similarly, right helical needle 260 is removed from head assembly 100 by using surgical tool 800 to grasp needle receiver 330 and release it from right upper spring latch 346 and right lower spring latch 348 of head assembly 100. Right suture 280 (hidden) is drawn through head assembly 100 (and vessels 702 and 704 if they are contained in head assembly 100). Helical needle 260 and right needle receiver 330 are removed by cutting right suture 280 (hidden in FIG. 27) with the surgical cutting tool, again taking care to provide a sufficient length of suture extending from head assembly 100 for knot tying later.

FIG. 28 is a top view of head assembly 100 in the open position. (Right and left needle receivers, 330 and 333, have been removed from head assembly 100 as described for FIG. 27.) The operator manually retracts release pin 128 to allow right frame 146 and left frame 147 to spring apart to the orientation depicted. The operator may next move head assembly 100 in the proximal (upward, as viewed in FIG. 28) direction to remove upper and lower tissue pins, 360 and 440, from the lumens of first and second vessels, 702 and 704, respectively.

Figures 29, 30:
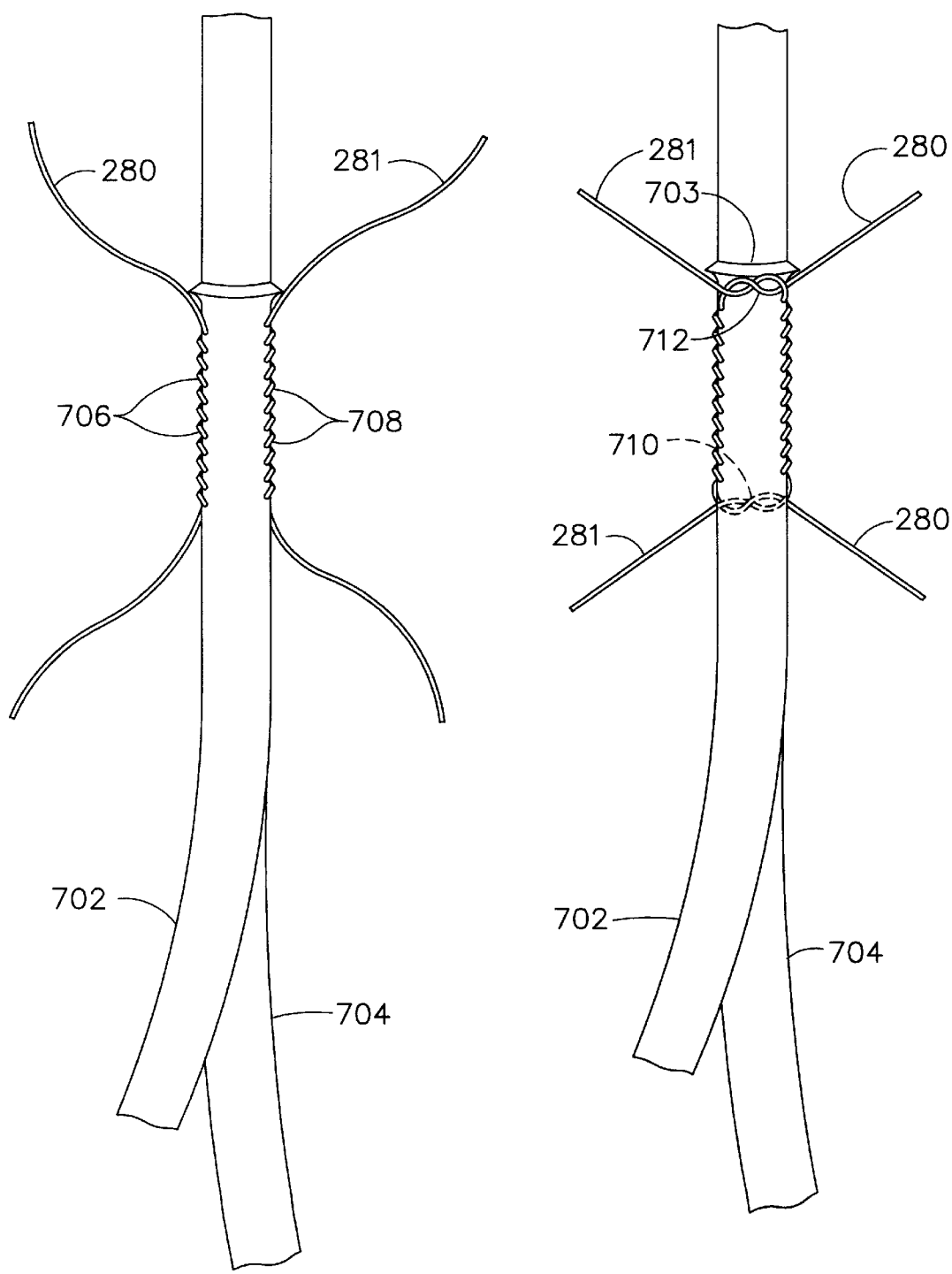
FIG. 29 is a top view of first vessel 702 joined to second vessel 704 by a plurality of right suture stitches 706 and plurality of left suture stitches 708.
FIG. 30 is the same view as FIG. 29, but with a proximal knot 712 and a distal knot 710 rally tied.

FIG. 29 is a top view of first and second vessels, 702 and 704, immediately after head assembly 100 has been removed as described for FIG. 28. First and second vessels, 702 and 704, are loosely held together by a plurality of right and left suture stitches, 706 and 708, of right and left sutures, 280 and 281, respectively.

FIG. 30 is a similar view as FIG. 29, showing a partially tied distal knot 710 and a partially tied proximal knot 712 in right and left sutures, 280 and 281. Distal knot 710 is first tied under first vessel 702 by applying a plurality of conventional, alternating suture throws. Proximal knot 712 is then tied over first vessel 702 by applying a plurality of conventional, alternating suture throws, thus closing open end 703 of first vessel 702. As proximal knot 712 is drawn together, plurality of right and left suture stitches, 706 and 708, are tightened to hold first and second vessels, 702 and 704, tightly together and sealing around the edges of the newly created passageway between them. The unneeded portions of right and left sutures, 280 and 281, are then trimmed off using a surgical cutting tool and the anastomosis is completed. The operator may also tie the knots in the reverse order, that is, proximal knot 712 may alternatively be tied before tying distal knot 710.

Figure 31:
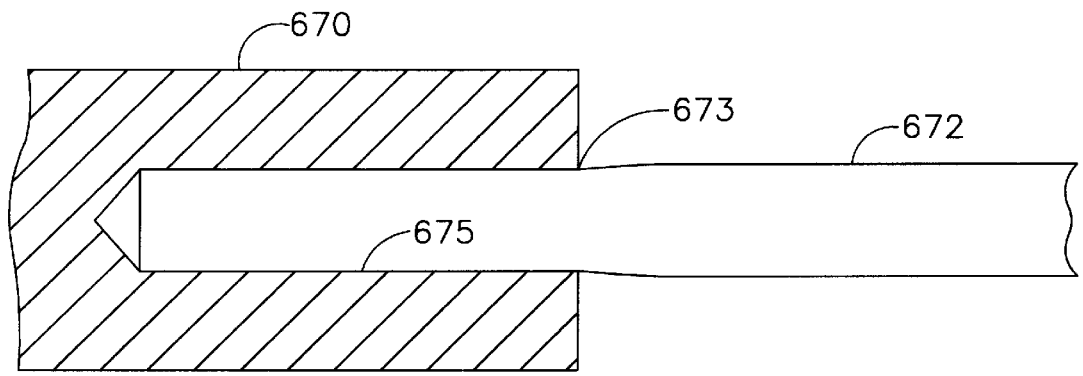
FIG. 31 is a side sectional view of a portion of a prior art needle 670 shown attached in a conventional manner to a prior art suture 672.

FIG. 31 is a sectional view of a prior art needle 670 conventionally attached to a suture 672. As is well-known in the art, there are a variety of methods for attaching a surgical needle to a suture. FIG. 31 depicts one method in which needle 670 having a needle hole 675 is crimped directly over suture 672. When suture 672 is pulled in a direction non-parallel to the longitudinal axis of needle 670, there is a stress concentration at a corner edge 673 of needle hole 675. With sufficient force, the strength of suture 672 is exceeded and suture 672 breaks next to corner edge 673.

Figure 32:
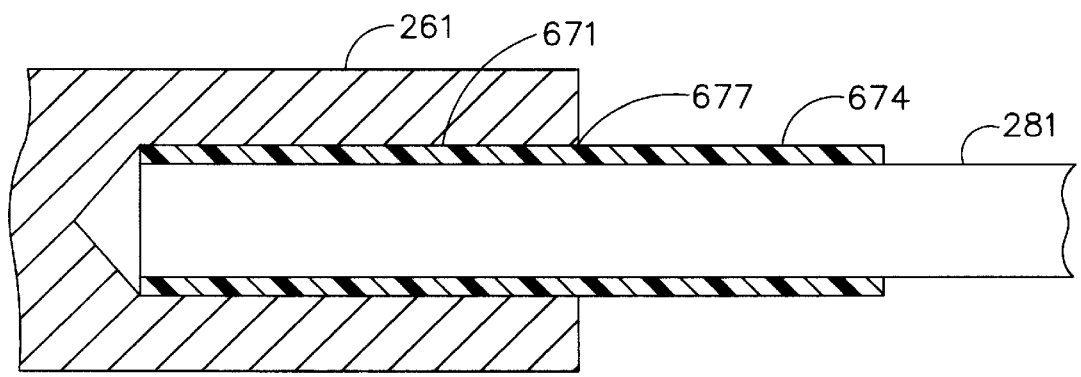
FIG. 32 is a side sectional view of a portion of left helical needle 261 of the present invention shown attached to left suture 281, and assembled with a stress relieving element 674.

FIG. 32 is a cross-sectional view of left helical needle 261 of the present invention. A stress relieving element 674 covers left suture 281 inside a left helical needle hole 671 and extending outside hole 671 a short (1–3 mm, for example) distance. Stress relieving element 674 provides an interface between needle 261, which may be made of, but is not limited to, a stainless steel, and suture 281, which may be made of, but is not limited to, a polymer or organic material that is much softer than stainless steel. Stress relieving element 674 is preferably a flexible plastic. A suitable material for stress relieving element 674 is a high performance, medical grade, natural colored, polyimide tubing (code 030-I) that is available from MicroLumen, Inc., 7930 Woodland Center Blvd., Tampa, Fla., U.S.A. 33614. The inner diameter of the 030-I polyimide tubing is 0.0031 inches (0.078 mm) and the wall thickness is 0.00040 inches (0.010 mm). When left suture 281 is pulled in a direction non-parallel to the longitudinal axis of needle 261, stress is not as concentrated at corner edge 677 as for the stress at corner edge 673 of the prior art needle 670 in FIG. 31. Therefore, the maximum off-axis pulling force that may be applied to suture 281 is much higher than for the prior art needle/suture combination in FIG. 31, everything else being equal. In the present invention, the stress relieving element 674 is particularly useful during the repeated rotations of right and left helical needles, 260 and 261, through head assembly 100. Stress relieving element 674, however, is not limited to use with the present invention, but is generally applicable to many other surgical needle/suture combinations.

While the applicant describes in this document a preferred embodiment of the present invention, it will be obvious to those skilled in the art that the applicant provides such an embodiment as an example only. Numerous variations and substitutions will now occur to those skilled in the art without departing from the spirit and scope of the appended claims.

What is claimed is:

1. An anastomosis device for attaching a first hollow vessel to a second hollow vessel, said device comprising:
   a. A handle for holding said device, and a head assembly, attached to said handle, for holding said first and second hollow vessels adjacent to each other, said head assembly having a distal end, a proximal end and a longitudinal axis therebetween;
   b. a longitudinal needle guide disposed longitudinally along said head assembly adjacent to said vessels, and a helical needle comprising a plurality of spaced apart helical coils, said helical needle having a suture attached to a proximal end thereof, disposed within said head assembly at its proximal end, said needle guide having a plurality of ribs disposed along its length, said ribs being spaced apart at substantially the same distance as the helical coils are spaced from one another; and
   c. an actuator on said handle for actuating a needle driver, said needle driver coupled to said head assembly, said needle driver comprising a flexible rotatable member operated by said actuator for rotating and driving said needle distally along said needle guides and through said first and second hollow vessels, said flexible rotatable member comprising an inner shaft, an intermediate coiled spring surrounding said inner shaft, and an outer wire mesh surrounding said coiled spring.

2. The device of claim 1 wherein said plurality of ribs comprises a plurality of longitudinally spaced ribs having spaces therebetween, and wherein said needle driver further comprises a longitudinal roller attached to said flexible rotatable member, said longitudinal roller is substantially coextensive with said needle guide, said longitudinal roller having a plurality of annular rings that mesh into said spaces between said spaced ribs, whereby said longitudinal roller makes frictional contact with said annular rings and rotates so as to drive said needle distally.

3. The device of claim 1 wherein said flexible rotatable member has substantially no shape memory.

4. The device of claim 1 wherein said outer wire mesh is braided wire.

5. The device of claim 4 wherein said braided wire is attached to said coiled spring under tension.

6. The device of claim 1 wherein said coiled spring is substantially compressed.

7. The device of claim 1 wherein said flexible rotatable member is substantially resistant to elongation during actuation of said actuator.

8. An anastomosis device for attaching a first hollow vessel to a second hollow vessel, said device comprising:

a. A handle for holding said device, and a head assembly, attached to said handle, for holding said first and second hollow vessels adjacent to each other, said head assembly having a distal end, a proximal end and a longitudinal axis therebetween, said head further including a plow disposed therein for incising at lest one of said hollow vessels so as to create a passageway between said vessels;

b. a longitudinal needle guide disposed longitudinally along said head assembly adjacent to said vessels, and a helical needle comprising a plurality of spaced apart helical coils, said helical needle having a suture attached to a proximal end thereof, disposed within said head assembly at its proximal end, said needle guide having a plurality of ribs disposed along its length, said ribs being spaced apart at substantially the same distance as the helical coils are spaced from one another; and c. an actuator on said handle for actuating a needle driver, said needle driver coupled to said head, said needle driver comprising a flexible rotatable member operated by said actuator for rotating and driving said needle distally along said needle guides and through said first and second hollow vessels, said flexible rotatable member comprising an inner shaft, an intermediate coiled spring surrounding said inner shaft, and an outer wire mesh surrounding said coiled spring.

9. The device of claim 1 wherein said plurality ribs comprises a plurality of longitudinally spaced ribs having spaces therebetween, and wherein said needle driver further comprises a longitudinal roller attached to said flexible rotatable member, said longitudinal roller is substantially coextensive with said needle guide, said longitudinal roller having a plurality of annular rings that mesh into said spaces between said spaced ribs, whereby said longitudinal roller makes frictional contact with said annular rings and rotates so as to drive said needle distally.

10. The device of claim 1 wherein said flexible rotatable member has substantially no shape memory.

11. The device of claim 1 wherein said outer wire mesh is braided wire.

12. The device of claim 4 wherein said braided wire is attached to said coiled spring under tension.

13. The device of claim 1 wherein said coiled spring is substantially compressed.

14. The device of claim 1 wherein said flexible rotatable member is substantially resistant to elongation during actuation of said actuator.

* * * * *